United States Patent [19]

Marsh, Jr. et al.

[11] Patent Number: 6,057,131
[45] Date of Patent: May 2, 2000

[54] PREPARATION AND USE OF SIALYLATED GLYCOFORMS OF SOLUBLE COMPLEMENT RECEPTOR 1 (CR1)

[75] Inventors: Henry C. Marsh, Jr., Reading, Mass.; Richard A. G. Smith, Relgate Surrey, United Kingdom; Chang-Jing Grace Yeh, Newton; John Lifter, Wellesly, both of Mass.; Anne Mary Freeman, Bucks, United Kingdom; Michael L. Gosselin, Revere, Mass.

[73] Assignee: Avant Immunotherapeutics, Inc., Needham, Mass.

[21] Appl. No.: 09/186,827

[22] Filed: Nov. 5, 1998

Related U.S. Application Data

[62] Division of application No. 08/470,867, Jun. 6, 1995, Pat. No. 5,858,969, which is a division of application No. 07/927,099, Aug. 7, 1992, Pat. No. 5,456,909.

[51] Int. Cl.[7] .......................... C12N 15/12; C07K 14/47; A61K 38/17
[52] U.S. Cl. .............................. 435/69.1; 530/412; 514/8
[58] Field of Search .............................. 514/8; 530/412; 435/69.1

[56] References Cited

U.S. PATENT DOCUMENTS

| | | |
|---|---|---|
| 5,212,071 | 5/1993 | Fearon et al. . |
| 5,256,642 | 10/1993 | Fearon et al. . |
| 5,456,909 | 10/1995 | Marsh et al. . |
| 5,472,939 | 12/1995 | Fearon et al. . |
| 5,858,969 | 1/1999 | Marsh et al. .............................. 514/8 |

FOREIGN PATENT DOCUMENTS

| | | |
|---|---|---|
| 0319253 | 6/1989 | European Pat. Off. . |
| WO 89/09220 | 10/1989 | WIPO . |
| WO 91/05047 | 4/1991 | WIPO . |
| WO 92/10205 | 6/1992 | WIPO . |

OTHER PUBLICATIONS

Mulligan et al., 1992, "Lung Injury After Deposition of IgA Immune Complexes", *J. Immunol.* 148: 3086–3092.

Mulligan et al., 1992, "Protective Effects of Soluble CR1 in Complement and Neutrophil–Mediated Tissue Injury", *J. Immunol.* 148: 1479–1485.

Pruitt et al., 1991, "The Effects of Soluble Complement Receptor Type 1 on Hyperacute Xenograft Rejection", *Transplantation* 52:868–873.

Pruitt and Bolinger, 1991, "The Effects of Soluble Complement Receptor type 1 on Hyperacute Allograft Rejection", *J. Surg. Res.* 50:350–355.

Yeh et al., 1991, "Recombinant Soluble Human Complement Receptor Type 1 Inhibits Inflammation in the Reversed Passive Arthus Reaction in Rats", *J. Immunol.* 146:250–256.

Weisman et al., 1990, "Soluble Human Complement Receptor Type 1: In Vivo Inhibitor of Complement Suppressing Post Ischemic Myocardial Inflammation and Necrosis", *Science* 249: 146–151.

Yoon and Fearon, 1985, "Characterization of a Soluble Form of the C3b/C4b Receptor (CR1) in Human Plasma", *J. Immunol.* 134:3332–3338.

Krych et al., 1989, "A Secreted Small Form of Human Complement C3b/C4b Receptor (CR1) That Binds to C4b but not C3b",*F.A.S.E.B. J.* 3: A368.

Klickstein et al., 1988, "Identification of Distinct C3b and C4b Recognition Sites in the Human C3b/C4b Receptor (CR1,CD35) by Deletion Mutagenesis", *J. Exp. Med.* 168: 1699–1717.

Hourcade et al., 1988, "Identification of an Alternative Polyadenylation Site in the Human C3b/C4b Receptor (Complement Receptor type 1) Transcriptional Unit and Prediction of a Secreted Form of Complement Receptor Type 1", *J. Exp. Med.* 168: 1255–1270.

Klickstein, et al., 1987, "Human C3b/C4b Receptor (CR1)", *J. Exp. Med.* 165: 1095–1112.

Wong et al., 1985, "Rapid Purification of the Human C3b/C4b Receptor (CR1) by Monoclonal Antibody Affinity Chromatography" *J. Immunol. Methods* 82:303–313.

Lublin et al., 1986, "Influence of Glycosylation on Allelic and Cell–Specific Mr. Variation, Receptor Processing, and Ligand Binding of the Human Complement C3b/C4b Receptor", *J. Biol. Chem.* 261:5736.

Sim, 1985, "Large–Scale Isolation of Complement Receptor Type 1 (CR1) From Human Erythrocytes", *Biochem J.* 232: 883–889.

Skubitz and Snook, 1987, "Monoclonal Antibodies that Recognize Lacto–N–Fucopentaose III (CD15) React with the Adhesion–Promoting Glycoprotein Family (LFA–1/HMAC–1/GP 150,95) and CR1 on Human Neutrophils", *J. Immunol.* 139: 1631–1639.

West, 1986, "Current Ideas on the Significance of Protein Glycosylation", *Mol. Cell. Biochem.* 72: 3–20.

Goochee and Monica, 1990, "Environmental Effects on Protein Glycosylation", *Bio/Technology* 8: 421–427.

Takenchi et al., 1988, "Comparative Study of the Asparagine–Linked Sugar Chains of Human Erythroproteins Purified from Urine and the Culture Medium of Recombinant Chinese Hamster Ovary Cells", *J. Biol. Chem.* 263:3657–3663.

Parekh et al., 1989, "N–glycosylation and the Production of Recombinant Glycoproteins", *Trends in Biotechnol.* 7: 117–122.

(List continued on next page.)

*Primary Examiner*—David L. Fitzgerald
*Attorney, Agent, or Firm*—Leon R. Yankwich

[57] ABSTRACT

Provided are methods of making preparations of recombinant soluble Complement Receptor type 1 (sCR1) defined with respect to the distribution of sCR1 glycoforms and therapeutic methods using them. The preparations are suitable for treatment of allograft or xenograft rejection, diseases involving inflammation or inappropriate complement activation, and thrombotic or shock state conditions. Preferred methods employ sCR1 glycoforms that are sialylated, have a pI of $\leq 5.1$, or have a sialic acid: mannose molar ratio of $\geq 0.25$.

28 Claims, 6 Drawing Sheets

OTHER PUBLICATIONS

Makrides et al. 1992, "Cell Surface Expression of the C3b/C4b Receptor (CR1) Protects Chinese Hamster Ovary Cells from Lysis by Human Complement", *J. Biol. Chem.* 267: 24754–24761.

Stanley et al., 1988, "The LEC11 Chinese Hamster Ovary Mutant Synthesized N–Linked Carbohydrates Containing Sialylated, Fucosylated Lactosamine Units", *J. Biol. Chem.* 263:11374–11381.

Paulson, 1989, "Glycoproteins: What Are The Sugar Chains For?" *Trends in Biochem. Sci.* 14: 272–276.

Goochee et al., 1991, "The Oligosaccharides of Glycoproteins: Bioprocess Factors Affecting Oligosaccharide Structure and Their Effect on Glycoprotein Properties", *Biotechnolgy* 9: 1347–1355.

Kobata, Akira, 1992, "Structures and Functions of the Sugar Chains of Glycoproteins",*Eur. J. Biochem.* 209: 483–501.

Morgan, B.P., *Complement: Clinical Aspects and Relevance to Disease*, (London: Academic Press), excerpts from chapters 5–11, 1990.

Frank, M.M., "Complement in the pathophysiology of human disease," *New Engl. J. Med.* 316: 1525–29, 1987.

Niculescu, F., et al., "Activation of human terminal complement pathway in atherosclerosis," *Clin. Immunol. Immunopathol.* 52: 868–73, 1987.

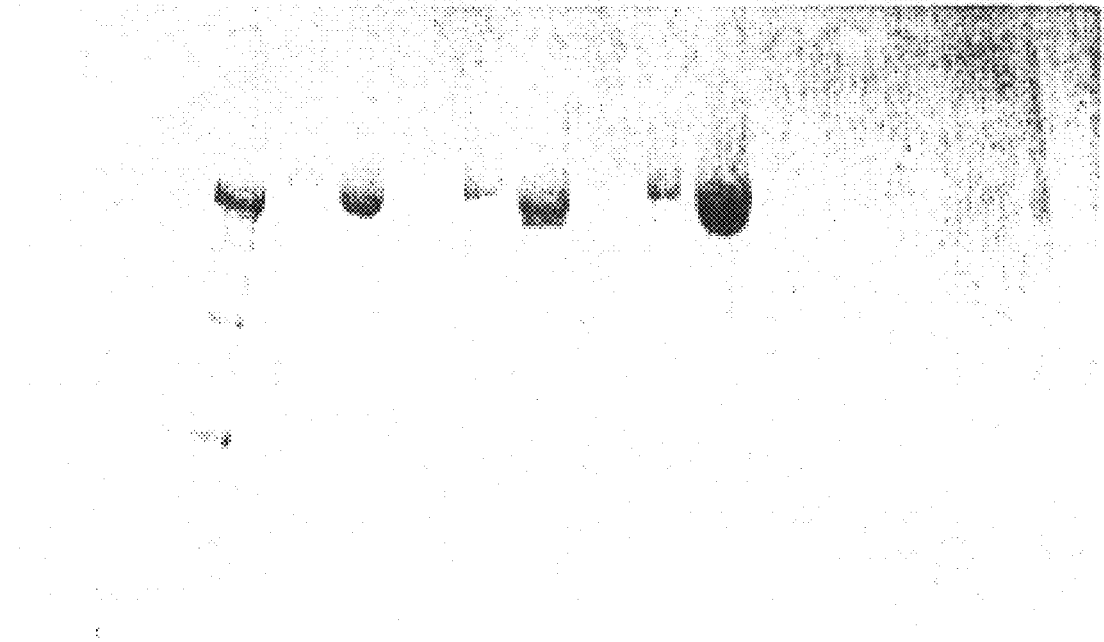

% NEUTRAL=64%
% ACIDIC=36%

% NEUTRAL=31%
% ACIDIC=69%

PREPARATION AND USE OF SIALYLATED GLYCOFORMS OF SOLUBLE COMPLEMENT RECEPTOR 1 (CR1)

This application is a division of U.S. application Ser. No. 08/470,867 filed Jun. 6, 1995, now U.S. Pat. No. 5,858,969, which is a division of U.S. application Ser. No. 07/927,099 filed Aug. 7, 1992, now U.S. Pat. No. 5,456,909.

FIELD OF THE INVENTION

The present invention relates to novel glycoforms of the soluble complement receptor type 1 (sCR1), and their uses in the diagnosis and therapy of disorders involving complement activity and various inflammatory and immune disorders. The invention also provides methods of producing, detecting, and purifying such glycoforms.

BACKGROUND OF THE INVENTION

The Complement System

Constituting about 10% of the globulins in normal serum, the complement system is composed of many different proteins that are important in the immune system's response to foreign antigens. The complement system becomes activated when its primary components are fragmented and the fragments, alone or with other proteins, activate additional complement proteins resulting in a proteolytic cascade. Activation of the complement system leads to increased vascular permeability, chemotaxis of phagocytic cells, activation of inflammatory cells, opsonization of foreign particles, direct killing of cells and tissue damage. Activation of the complement system may be triggered by antigen-antibody complexes (the classical pathway) or for example, by lipopolysaccharides present in cell walls of pathogenic bacteria (the alternative pathway).

The Membrane Bound Complement Receptor Type 1

Complement receptor type 1 (CR1) is present on the membranes of erythrocytes, monocytes/macrophages, granulocytes, B cells, some T cells, splenic follicular dendritic cells, and glomerular podocytes. CR1 binds to the complement components C3b and C4b and has also been referred to as the C3b/C4b receptor. The structural organization and primary sequence of CR1 is known (Klickstein et al., 1987, J. Exp. Med. 165:1095–1112, Klickstein et al., 1988, J. Exp. Med. 168:1699–1717; Hourcade et al., 1988, J. Exp. Med. 168:1255–1270). It is composed of 30 short consensus repeats (SCRs) that contain 60–70 amino acids. In each SCR, 29 of the average 65 amino acids are conserved. Each SCR has been proposed to form a three dimensional triple loop structure through disulfide linkages with the third and first and the fourth and second half-cystines in disulfide bonds. CR1 is further arranged as 4 long homologous repeats (LHRs) of 7 SCRs each. Following a leader sequence, which is post-translationally removed, the CR1 molecule consists of the most N-terminal LHR-A comprising a C4b binding domain, the next two repeats, LHR-B and LHR-C comprising C3b binding domains, and the most C terminal LHR-D followed by 2 additional SCRs, a 25 residue putative transmembrane region and a 43 residue cytoplasmic tail.

CR1 is a member of a protein superfamily characterized by this SCR homology. Some superfamily members that have C3/C4 binding function include CR2, C4 binding protein, factor H, factor B, and C2, while proteins lacking this function include interleukin-2 receptor, β2-glycoprotein I, C1r, haptoglobin α chain, and factor XIIIb.

CR1 is known to be a glycoprotein and its deduced amino acid sequence has 25 potential sites for N-linked glycosylation (amino acid consensus sequence NXS or NXT) in the extracellular region. Only 6–8 of the available sites were reported to be linked to oligosaccharides (Sim, 1985, Biochem. J. 232:883). A non-glycosylated form of CR1 has been produced in the presence of tunicamycin and showed reduced binding to iC3 (Lublin et al., 1986, J. Biol. Chem. 261:5736). The N-terminus of the glycoprotein appears to be blocked.

Thus far, four different CR1 allelic forms or allotypes have been identified, and differ in size by 30–50 kDa increments. The gene frequencies of these allotypes differ in the human population (Holer et al. 1987, Proc. Natl. Acad. Sci. U.S.A. 84:2459–2463). The F (or A) allotype is composed of 4 LHRs and has a molecular weight of about 250 kDa; the larger S (or B) allotype, with a molecular weight of about 290 kDa, contains a fifth LHR that is a chimera of the 5' half of LHR-B and the 3' half of LHR-A and is predicted to have a third C3b binding site (Wong et al., 1989, J. Exp. Med. 169:847). The smallest F' (or C) allotype, most likely arising from the deletion of LHR-B and one C3b binding site, has increased prevalence in patients with systemic lupus erythematosus (SLE) (Van Dyne et al., 1987, Clin. Exp. Immunol. 68:570; Dykman et al., 1983, Proc. Natl. Acad. Sci. U.S.A. 80:1698).

Soluble Complement Receptor Type 1

A naturally occurring soluble form of CR1 has been detected in the plasma of normal individuals and certain individuals with SLE (Yoon et al., 1985, J. Immunol. 134:3332–3338). Its characteristics are similar to those of erythrocyte (cell-surface) CR1, both structurally and functionally. Hourcade et al., 1988, J. Exp. Med. 168:1255–1270) also observed an alternative polyadenylation site in the human CR1 transcriptional unit that was predicted to produce a secreted form of CR1. The mRNA encoded by this truncated sequence comprises the first 8.5 SCRs of CR1, and encodes a protein of about 80 kDa which includes the C4b binding domain. When a cDNA corresponding to this truncated sequence was transfected into COS cells and expressed, it demonstrated the expected C4b binding activity but did not bind to C3b (Krych et al., 1989, FASEB J. 3:A368). Krych et al. also observed a mRNA similar to the predicted one in several human cell lines and postulated that such a truncated soluble form of CR1 with C4b binding activity may be synthesized in humans.

Several soluble fragments of CR1 have also been generated via recombinant DNA procedures by eliminating the transmembrane region from the DNAs being expressed (Fearon et al., Intl. Patent Publ. WO 89/09220, Oct. 5, 1989; Fearon et al., Intl. Patent Publ. WO 91/05047, Apr. 18, 1991). The soluble CR1 fragments were functionally active, bound C3b and/or C4b and demonstrated factor I cofactor activity depending upon the regions they contained. Such constructs inhibited in vitro the consequences of complement activation such as neutrophil oxidative burst, complement mediated hemolysis, and C3a and C5a production. A soluble construct, sCR1/pBSCR1c, also demonstrated in vivo activity in a reversed passive Arthus reaction (Fearon et al., 1989, 1991, supra; Yeh et al., 1991, J. Immunol. 146:250), suppressed post-ischemic myocardial inflammation and necrosis (Fearon et al., supra; Weisman et al., Science, 1990, 249:146–151) and extended survival rates following transplantation (Pruitt & Bollinger, 1991, J. Surg. Res 50:350; Pruitt et al., 1991 Transplantation 52; 868). Furthermore, co-formulation of the soluble product of vector sCR1/pBSCR1c with p-anisoylated human plasminogen-streptokinase-activator complex (APSAC) resulted in similar anti-hemolytic activity as the sCR1/pBSCR1c product alone, indicating that the combination of the complement inhibitor sCR1 with a thrombolytic agent was feasible (Fearon et al., supra).

Each of International Patent Publication Number WO 89/09220, published Oct. 5, 1989, and WO 91/05047, published Apr. 18, 1991, are incorporated by reference herein in their entirety.

SUMMARY OF THE INVENTION

The present invention relates to novel glycoforms of soluble complement receptor 1 protein (sCR1) and their uses in the therapy of disorders involving complement activity and various inflammatory and immune disorders.

The present inventors have discovered that, under certain conditions of production, novel glycoforms of sCR1 may be obtained which exhibit the desirable properties of prolonged clearance from the blood while retaining significant functional activity. A long functional half-life permits simplified, bolus-dose administration and contributes to potency in vivo.

The present inventors have applied various purification methods to resolve and enrich particular sCR1 glycoforms. Thus, the present invention provides a soluble complement receptor 1 (sCR1) glycoprotein molecule containing one or more complex oligosaccharide structures, each of which structures are terminated with on average one or more sialic acid residues.

In one embodiment is provided a preparation of a sCR1 glycoprotein wherein at least 40% of the molecules contain one or more complex oligosaccharide structures, each of which oligosaccharide structures contain on average at least one terminal sialic acid residue. Preferably, at least 70% of the molecules contain one or more complex oligosaccharide structures, each of which contain on average at least one terminal sialic acid residue.

In one embodiment, a sCR1 preparation comprises sCR1 glycoprotein molecules, in which predominant glycoforms exhibit an isoelectric point, pI, less than or equal to 5.1 as determined by chromatofocusing, wherein the pI increases after neuraminidase treatment.

In another embodiment, the sCR1 preparation comprises a sCR1 glycoprotein wherein the molar ratio of sialic acid to mannose in the glycoprotein is greater than or equal to 0.25.

Preferably a sCR1 preparation according to the present invention has at least 25% of the functional complement-inhibitory activity of deglycosylated sCR1.

In a preferred embodiment of the molecule or preparation of the present invention, the protein backbone of the sCR1 glycoprotein contains LHR-A, LHR-B, LHR-C, LHR-D, SCR29, and SCR30 regions up to and including the first alanine residue of the transmembrane region.

The present invention is also directed to a pharmaceutical composition comprising a therapeutically effective amount of a sCR1 glycoprotein molecule, as above, and a pharmaceutically acceptable carrier or excipient. In one embodiment, the pharmaceutical composition further comprising a therapeutically effective amount of a thrombolytic agent.

Preferably, the thrombolytic agent is selected from the group consisting of:

(a) a plasminogen activator or a mutein thereof;
(b) anisoylated plasminogen-streptokinase-activator complex (APSAC);
(c) single-chain urokinase;
(d) two-chain urokinase;
(e) streptokinase;
(f) a fibrinolytically active hybrid protein which comprises one chain of a first two-chain protease linked to one chain of a second two-chain protease, at least one of said first or second protease having fibrinolytic activity, such that said hybrid protein has a catalytic site essential for fibrinolytic activity which is optionally blocked by a removable blocking group; and
(g) a reversibly blocked in vivo fibrinolytic enzyme wherein the catalytic site essential for fibrinolytic activity in said enzyme is blocked by a group which is removable by hydrolysis at a rate such that the pseudo first order rate constant for hydrolysis is in the range $10^{-6}$ sec$^{-1}$ to $10^{-3}$ sec$^{-1}$ in an isotonic aqueous solution at pH 7.4 at 37° C.

The present invention also provides a method of treating a disease or disorder associated with inflammation or inappropriate complement activation comprising administering to a subject in need of such treatment a therapeutically effective amount of a sCR1 pharmaceutical composition as above.

Also provided is a method of treating a thrombotic condition, comprising administering to a subject in need of such treatment an effective amount of a sCR1 pharmaceutical composition or preferably, a pharmaceutical composition as above including a thrombolytic agent.

In the above methods, the subject is preferably a human.

The present invention is further directed to a process for preparing a sCR1 glycoprotein or sCR1 preparation, as above, comprising:

(a) expressing a DNA molecule encoding the protein backbone of the sCR1 in a mammalian host cell in culture under conditions wherein cell growth is not limited by nutrient supply, and wherein the host cell is capable of sialylation of the oligosaccharide chains; and
(b) isolating the sCR1 glycoprotein from the culture.

In a preferred embodiment, the process further comprises the step of:

(c) isolating sialic acid-containing molecules from the material obtained in step (b).

In the above methods, preferred culture conditions include a fluidized bed bioreactor, hollow fiber bioreactor, roller bottle culture or stirred tank bioreactor system, in the latter two systems, with or without cell microcarriers.

The sCR1 glycoprotein product of the above cell culture may be purified by affinity, size exclusion, ion-exchange and/or hydrophobic interaction chromatography. Enrichment for sialic acid-containing molecules is preferably achieved by ion-exchange soft gel chromatography or HPLC using cation- or anion-exchange resins, with collection of the more acidic fraction. Sialic acid-containing molecules can also be isolated by chromatofocusing or lectin affinity chromatography.

Preferably, the mammalian host cell is capable of expressing sialyl transferases at a level sufficient to ensure substantial sialylation of oligosaccharides in the expressed sCR1 glycoprotein. Suitable host cells include CHO lines, preferably the DUX B11 cell line.

ABBREVIATIONS AND DEFINITIONS

APSAC=anisoylated plasminogen-streptokinase-activator complex
pI=isoelectric point
HPLC=high performance liquid chromatography IH50%=concentration yielding 50% inhibition of hemolysis
SRBC=sheep red blood cell
EIA=enzyme immunoassay
w/v=weight to volume ratio
v/v=volume to volume ratio
kDa=kilodalton
ELISA=enzyme linked immunosorbent assay
gu=glucose units
SDS-PAGE=sodium dodecyl sulfate polyacrylamide gel electrophoresis
glycoforms=species of a glycoprotein, such as the soluble CR1 glycoprotein of the present invention, that are characterized by their carbohydrate content, chromatographic behavior, and/or charge
TP10HD=a particular soluble CR1 construct containing LHR-A, LHR-B, LHR-C, LHR-D, SCR29, SCR30 regions up to and including the first alanine residue of the transmembrane region; TP10HD corresponds to the CR1 coding sequences in plasmid pBSCR1c (Fearon et al., Int'l. Patent Publication No. WO 89/09220 (Oct. 5, 1989)
TP10HD-CC=TP10HD produced by cells cultured in a fluidized bed perfusion bioreactor and purified by combination chromatography, as described herein
TP10HD-CCW=the weakly cationic form of TP10HD-CC isolated by preparative HPLC cation exchange chromatography
TP10HD-CCS=the strongly cationic form of TP10HD-CC isolated by preparative HPLC cation exchange chromatography
TP10HD-CX=TP10HD produced by cells cultured in a hollow fiber bioreactor and purified by HPLC cation exchange chromatography (Fearon et al., supra).
TP10HD-CXD=TP10HD-CX enzymatically deglycosylated with n-glycanase

BRIEF DESCRIPTION OF THE DRAWINGS

FIG. 1A TP10HD material purified by affinity chromatography, contained multiple glycoforms, the predominant glycoforms were strongly cationic (i.e. eluting at about 125 mM NaCl).

FIG. 1B TP10HD material purified by combination chromatography contained multiple glycoforms; the ratios of concentration of weakly cationic to strongly cationic glycoforms ranged from 70:30 to 80:20.

FIG. 1C TP10HD purified by HPLC cation exchange chromatography contained only the strongly cationic glycoform.

FIG. 3 shows a SDS-PAGE gel pattern of the material eluted from the S-Sepharose column of FIG. 2. Lane 1: high molecular weight standards; Lanes 5 and 8: S-Sepharose Pool 1 (2.4 μg each); Lanes 6 and 9: S-Sepharose Pool 2 (5.0 and 6.7 μg, respectively)

FIGS. 4C and 4D show the patterns after neuraminidase treatment.

DETAILED DESCRIPTION OF THE PREFERRED EMBODIMENTS

Figure 1A:
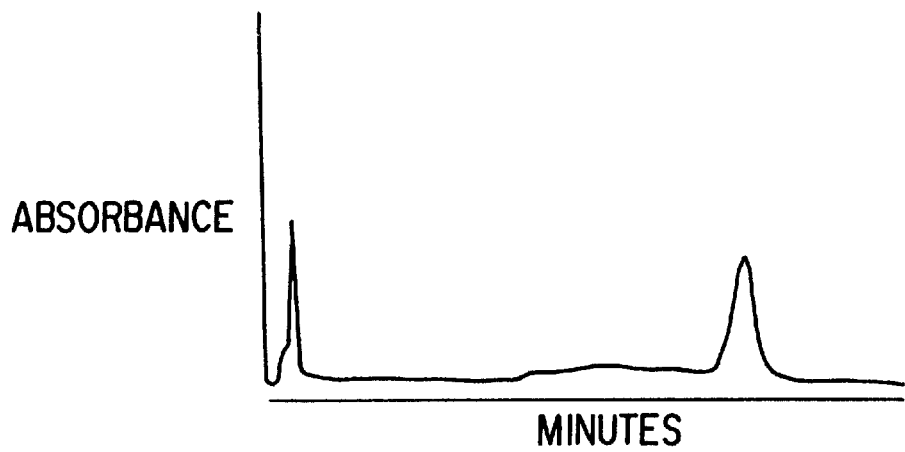
FIGS. 1A–1C are a series of absorbance tracings at 280 nm showing results of analytical HPLC of TP10HD preparations purified in different ways. A modification of the Hydropore-SCX HPLC purification method was used to demonstrate the existence of TP10HD glycoforms.

The present invention relates to novel glycoforms of soluble complement receptor 1 protein (sCR1) and their uses in the diagnosis or therapy of disorders involving complement activity and various inflammatory and immune disorders.

Soluble complement receptor 1 (sCR1) is defined herein as a soluble form of human CR1 containing all 30 extracellular SCR domains.

sCR1 and processes by which it can be prepared are disclosed in International Patent Publications WO 89/09220 (Oct. 5, 1989) and WO 91/05047 (Apr. 18, 1991). Preferably, the sCR1 material is prepared by culturing recombinant Chinese hamster ovary (CHO) DUX B11 cells in a fluidized bed perfusion bioreactor (See WO 91/05047, supra).

The sCR1 glycoforms of the present invention are characterized by their carbohydrate content, chromatographic behavior and/or charge. Accordingly, the present invention provides:

(1) sCR1 comprising a complex oligosaccharide terminated by one or more residues of sialic acid;

(2) sCR1 having an isoelectric point, pI≦5.1 as measured by chromatofocusing, in which the pI increases after neuraminidase treatment;

(3) sCR1 preparations in which at least 40% of the sCR1 molecules comprise a complex oligosaccharide terminated by one or more residues of a sialic acid;

(4) sCR1 preparations preferably comprising at least 70% of sialic acid-terminated molecules;

(5) sCR1 preparations in which the molar ratio of sialic acid to mannose is ≧0.25; and (6) preferred sCR1 glycoforms and preparations having at least 25% of the functional anti-complement activity of non-glycosylated sCR1.

The preferred glycoproteins are those which contain oligosaccharides similar to, or identical with, the oligosaccharides which occur naturally in human glycoproteins. The advantages of a sCR1 preparation having such oligosaccharides include a lower risk of their being immunogenic upon administration to a human.

The sCR1 glycoforms and preparations of the present invention are also characterized by their functional activity. Thus they preferably exhibit any one or more of the activities associated with sCR1 molecules, including but not limited to:

(1) binding to monomeric and/or polymeric C3b and/or C4b or C4ma;

(2) prevention of C3a or C5a production in complement-activated serum;

(3) factor I cofactor activity;

(4) inhibition of complement-induced neutrophil oxidative burst; and (5) inhibition of complement-mediated hemolysis.

Culturing, Purification, and Enrichment of sCR1 Glycoforms

The sCR1 glycoforms and preparations of the present invention may be produced by growing cells which express recombinant sCR1-encoding DNA under a variety of cell culture conditions, including but not limited to a fluidized bed bioreactor, hollow fiber bioreactor, roller bottle culture or stirred tank bioreactor system, in the latter two systems, with or without cell microcarriers.

The sCR1 glycoforms of the present invention may be obtained by expressing DNA encoding sCR1, or encoding fragments of sCR1 in a mammalian host cell. Preferably, the mammalian host cell is capable of expressing a functional sialyl transferase which results in production of an sCR1 glycoform containing oligosaccharide chains which preferably have one or more terminal sialic acid residues. Suitable host cells according to the present invention include CHO lines, preferably the DUX B11 cell line.

The cell culture conditions are selected to achieve the desired level of sialylation. Process parameters which influence the degree of sialylation include oxygen level and glucose level. Cell density, time, and storage conditions such as temperature also influence sialylation.

sCR1 glycoforms containing 2 or more sialic acid residues per complex oligosaccharide structure have longer clearance rates in vivo. The clearance rate of the preparation may thus be manipulated within broad limits by the overall degree of sialylation of the preparation. The effect of carbohydrate content on serum (or plasma) clearance correlates weakly with functional activity; deglycosylation leads to rapid plasma clearance, but minimal increases in in vitro functional activity.

The expressed sCR1 glycoforms produced in these cultures may be purified conventionally, for example, by affinity, size exclusion, ion-exchange and/or hydrophobic interaction chromatography (HIC). Several CR1-specific antibodies are available for use affinity chromatography (Changelian et al., 1985, J. Immunol. 134:1851).

A number of matrices may be employed in the preparation of HIC columns, the most extensively used is agarose. Silica and organic polymer resins may be used. Useful hydrophobic ligands include, but are not limited, to alkyl groups having from about 2 to about 10 carbon atoms, such as a butyl, propyl, or octyl; or aryl groups such as phenyl. Conventional HIC products for gels and columns may be obtained commercially under the product names butyl-SEPHAROSE®, phenyl-SEPHAROSE® CL-4B, octyl-SEPHAROSE® FF and phenyl-SEPHAROSE® FF (Pharmacia LKB AB, Uppsala, Sweden); TOYOPEARL Butyl 650M (Fractogel TSK Butyl-650) or TSK-GEL phenyl-5PW (Tosoh Corporation, Tokyo, Japan); alkyl-agarose, wherein the alkyl group contains from 2–10 carbon atoms (Miles-Yeda, Rehovot, Israel); and Bakerbond WP-HI-propyl (J. T. Baker, Phillipsburg, N.J.).

It is also possible to prepare the desired HIC column using conventional chemistry. See, for example, Er-el, Z. et al. Biochem. Biophys. Res. Comm. 49:383 (1972); Ulbrich, V. et al. Coll. Czech, Chem. Commum. 9:1466 (1964)). The choice of a particular gel can be determined by one of ordinary skill in the art. In general the strength of the interaction of the protein and the HIC ligand increases with the chain length of the of the alkyl ligands but ligands having from about 4 to about 8 carbon atoms are suitable for most separations. Adsorption of the proteins to a HIC column is favored by high salt concentrations, but the actual concentrations can vary over a wide range depending on the nature of the protein and the particular HIC ligand chosen. In general, salt concentrations of between about 0.75 and about 2M ammonium sulfate or between about 1 and 4M NaCl are useful.

Elution, whether stepwise or in the form of a gradient, can be accomplished in a variety of ways: (a) by changing the salt concentration, (b) by changing the polarity of the solvent or (c) by adding-detergents.

HIC is particularly useful when used in combination with other protein purification techniques.

As is well-known in the art, for ion exchange chromatography various anionic or cationic substituents may be attached to matrices in order to form anionic or cationic supports. Anionic exchange substituents include diethylaminoethyl(DEAE), quaternary aminoethyl (QAE) and quaternary amine(Q) groups. Cationic exchange substituents include carboxymethyl (CM), sulfoethyl(SE), sulfopropyl (SP), phosphate (P) and sulfonate (S). Commercially available ion exchange materials include: cellulosic ion exchange resins such as DE23, DE32, DE52, CM-23, CM-32 and CM-52 (Whatman Ltd. Maidstone, Kent, UK); SEPHADEXr-based and cross-linked ion exchangers, for example, DEAE-, QAE-, CM-, and SP-SEPHADEX® and DEAE-, Q-, CM-and S-SEPHAROSE® (Pharmacia AB); DEAE- and CM- derivatized ethylene glycol-methacrylate copolymer such as TOYOPEARL DEAE-650S and TOYOPEARL CM-650S (Toso Haas Co., Philadelphia, Pa.).

Size exclusion or gel filtration chromatography separates on the basis of molecular size. Preferred matrix materials are chemically inert, rigid and highly porous. For large scale processes rigidity is most important in establishing overall flow rate. Gels developed more recently which have increased rigidity are preferred, for example, SEPHACRYL®, ULTROGEL®, FRACTOGEL®, SUPEROSE® and TOYOPEARL HW series matrices (Toso Haas).

The desired sCR1 glycoforms of the present invention may be enriched for sialic acid-containing molecules by ion-exchange soft gel chromatography or HPLC using cation- or anion-exchange resins, wherein the more acidic fraction is collected. The preferred matrix for separating sCR1 glycoforms is S-Sepharose. The S-Sepharose chromatography step may be applied early in the overall protein purification process. At that time, a desired sCR1 glycoform may be separated from other glycoforms and the remaining purification steps carried out on that glycoform. Alternatively, an additional S-Sepharose purification step, designed to resolve the glycoforms, may be performed at the end of a multistep protein purification process, as exemplified in Example V, below.

Specific sCR1 glycoforms may also be selected via lectin affinity chromatography or chromatofocusing.

The complex carbohydrate portion of the sCR1 glycoform may be readily analyzed if desired, by conventional techniques of carbohydrate analysis. Thus, for example, techniques such as lectin blotting, well-known in the art, reveal a low proportion of terminal mannose or other sugars such as galactose. Termination of mono-, bi-, tri-, or tetra-antennary oligosaccharide by sialic acids can also be confirmed by release of sugars from the protein using anhydrous hydrazine or enzymatic methods and fractionation of oligosaccharides by ion-exchange or size exclusion chromatography or other methods well-known in the art. In a further test for identity of the glycoform, the pI is measured, before and after treatment with neuraminidase to remove sialic acids. An increase in pI following neuraminidase treatment indicates the presence of sialic acids on the glycoform.

Therapeutic Uses of CR1 Glycoforms

The sCR1 glycoforms and preparations of this invention are useful in the treatment or diagnosis of many complement-mediated or complement-related diseases and disorders, including but not limited to those listed in Table 1.

TABLE 1

Disease and Disorders Involving Complement

Neurological Disorders multiple sclerosis
stroke
Guillain Barré Syndrome
traumatic brain injury
Parkinson's disease Disorders of inappropriate or Undesirable Complement Activation hemodialysis complications
hyperacute allograft rejection
xenograft rejection
interleukin-2 induced toxicity during IL-2 therapy Inflammatory Disorders Inflammation of autoimmune diseases
Crohn's Disease
adult respiratory distress syndrome
thermal injury including burns or frostbite Post-Ischemic Reperfusion Conditions myocardial infarction
balloon angioplasty
post-pump syndrome in cardiopulmonary bypass or renal hemodialysis
renal ischemia
Infectious Disease or Sepsis Immune Complex Disorders and Autoimmune Diseases rheumatoid arthritis
systemic lupus erythematosus (SLE)
SLE nephritis
proliferative nephritis
glomerulonephritis
hemolytic anemia
myasthenia gravis In a method of treating a disease or disorder associated with inappropriate complement activation or inflammation, a therapeutically active amount of a sCR1 glycoform or preparation is administered to a subject in need of such treatment. The preferred subject is a human.

An effective amount of a sCR1 glycoform for the treatment of a disease or disorder is in the dose range of 0.01–100 mg/kg; preferably 0.1 mg–10 mg/kg.

For administration, the sCR1 glycoform or preparation should be formulated into an appropriate pharmaceutical or therapeutic composition. Such a composition typically contains a therapeutically active amount of the sCR1 glycoform or preparation and a pharmaceutically acceptable excipient or carrier such as saline, buffered saline, dextrose, or water. Compositions may also comprise specific stabilizing agents such as sugars, including mannose and mannitol, and local anesthetics for injectable compositions, including, for example, lidocaine.

In order to inhibit complement activation and, at the same time, provide thrombolytic therapy, the present invention provides compositions which further comprise a therapeutically active amount of a thrombolytic agent. An effective amount of a thrombolytic agent is in the dose range of 0.01–10 mg/kg; preferably 0.1–5 mg/kg. Preferred thrombolytic agents include, but not limited to, streptokinase, human tissue type plasminogen activator and urokinase molecules and derivatives, fragments or conjugates thereof. The thrombolytic agents may comprise one or more chains that may be fused or reversibly linked to other agents to form hybrid molecules (EP-A-0297882 and EP 155387), such as, for example, urokinase linked to plasmin (EP-A-0152736), a fibrinolytic enzyme linked to a water-soluble polymer (EP-A-0183503). The thrombolytic agents may also comprise muteins of plasminogen activators (EP-A-0207589). In a preferred embodiment, the thrombolytic agent may comprise a reversibly blocked in vivo fibrinolytic enzyme as described in U.S. Pat. No. 4,285,932. A most preferred enzyme is a p-anisoyl plasminogen-streptokinase activator complex as described in U.S. Pat. No. 4,808,405, and marketed by SmithKline Beecham Pharmaceuticals under the Trademark EMINASE (e.g. generic name anistreplase, also referred to as APSAC; Monk et al., 1987, Drugs 34:25–49).

A preferred therapeutic composition for inhibiting complement activation or for combined therapy, as above, comprises a novel sCR1 glycoform or preparation of this invention which exhibits prolonged clearance from the blood while retaining significant functional activity. Such a prolonged functional half-life permits simplified, bolus-dose administration and contributes to potency in vivo. Preferred complement activation inhibitors in the therapeutic composition include the sCR1 glycoforms and preparations described above, for example:

(1) sCR1 glycoforms comprising a complex oligosaccharide terminated by one or more residues of a sialic acid;

(2) preparations having an isoelectric point, $pI \leq 5.1$ as determined by chromatofocusing, in which the pI is sensitive to neuraminidase treatment;

(3) preparations in which at least 40% of the sCR1 molecules comprise a complex oligosaccharide terminated by one or more residues of a sialic acid; or (4) sCR1 preparations having a molar ratio of sialic acid to mannose of $\geq 0.25$.

More preferably the therapeutically active sCR1 glycoforms and preparations should comprise at least 70% of sialic acid-terminated molecules and have at least 25% of the anti-complement activity of non-glycosylated sCR1. Further preferred therapeutically active complement activation inhibitors of the therapeutic compositions should comprise oligosaccharides similar to or identical with those naturally occurring in human glycoproteins.

Routes of administration for the individual or combined therapeutic compositions of the present invention include standard routes, such as, for example, intravenous infusion or bolus injection. Active complement blockers and thrombolytic agents may be administered together or sequentially, in any order.

The present invention also provides a method for treating a thrombotic condition, in particular acute myocardial infarction, in a human or non-human animal. This method comprises administering to a human or animal in need of this treatment an effective amount of a sCR1 glycoform or preparation according to this invention and an effective amount of a thrombolytic agent.

Also provided is the use of a sCR1 glycoform or preparation of this invention and a thrombolytic agent in the manufacture of a medicament for the treatment of a thrombotic condition in a human or animal. Such methods and uses may be carried out as described earlier (International Patent Publication WO 91/05047, incorporated herein by reference.)

This invention further provides a method for treating adult respiratory distress syndrome (ARDS) in a human or non-human animal. This method comprises administering to the patient an effective amount of a sCR1 glycoprotein or preparation according to this invention.

The invention also provides a method of delaying hyperacute allograft or hyperacute xenograft rejection in a human or non-human animal which receives a transplant by administering an effective amount of a sCR1 glycoform or preparation according to this invention.

Having now generally described the invention, the same will be more readily understood through reference to the following examples which are provided by way of illustration, and are not intended to be limiting of the present invention, unless specified.

EXAMPLE I

Production and Purification of TP10HD Preparations

TP10HD prepared from conditioned tissue culture medium is purified by affinity chromatography, HPLC (or non-HPLC) cation exchange chromatography, and a combination of cation exchange, hydrophobic interaction and size exclusion chromatographies.

Sources of Conditioned Cell Culture Medium

A. Hollow Fiber Bioreactor

Recombinant CHO DUX B11 cells expressing the sCR1 gene product TP10HD (Fearon et al., 1989, 1991, supra) were inoculated into a hollow fiber bioreactor utilizing a model IV-L, 30,000 dalton molecular weight cut off cartridge (Cell-Pharm Cell Culture system I, CD Medical, Miami Lakes, Fla.) in a suitable growth medium, for example CHO-1 complete media system (Ventrex Laboratories, Inc. Portland, Me.) supplemented with glutamine (GIBCO, Grand Island, N.Y.) and 1–10% fetal bovine serum (HyClone Laboratories, Inc. Logan, Utah), and operated according to the manufacturer's instructions. The synthesized TP10HD was secreted into the growth medium and because of its large molecular weight, approximately 200 kDa, was retained within the cell compartment of the reactor cartridge. At 1–3 day intervals, the conditioned medium from within the cell compartment was removed, the contaminating cells and cellular debris removed by centrifugation and the clarified conditioned medium was dispensed into disposable plastic laboratory vessels and maintained at 2–8° C. until purification. Under these conditions, conditioned medium contained up to 500 μg/ml TP10HD.

B. Roller Bottle Cell Cultures

Recombinant CHO DUX B11 cells expressing TP10HD were inoculated into roller bottles in a suitable growth medium, for example a serum free formulation made from a mixture of Hams F12 and DMEM (JHR Biosciences, Inc., Denver, Pa.) supplemented with glutamine (GIBCO, Grand Island, N.Y.), bovine serum albumin, human transferrin and bovine insulin (Pentex-Miles Inc., Kankakee, Ill.; Intergen, Purchase, N.Y.). After the culture had become established, approximately three days, indicated by a change in medium color from pink to yellow, approximately 10 ml of collagen microcarriers (Verax Corporation, Lebanon, N.H.) were added along with fresh medium. At 3 day intervals one-half the medium (approximately 150 ml) was replaced. Cells and cellular debris were removed from the conditioned medium by filtration and the clarified conditioned medium was dispensed into disposable plastic laboratory vessels and stored at or below −70° C. until purification. Under these conditions, conditioned medium contained approximately 15 μg/ml TP10HD.

C. Fluidized Bed Perfusion Bioreactor

Recombinant CHO DUX B11 cells expressing TP10HD were inoculated into a fluidized bed perfusion bioreactor (System S200 and System S2000, Verax Corporation, Lebanon, N.H.) in a suitable growth medium, for example a serum free formulation made from a mixture of Hams F12 and DMEM supplemented with glutamine (GIBCO, Grand Island, N.Y.), bovine serum albumin, human transferrin and bovine insulin (Pentex-Miles Inc., Kankakee, Ill.; Intergen, Purchase, N.Y.) and the bioreactor was operated according the manufacturer's instructions. At approximately 2 day intervals, the collected conditioned medium was removed from the bioreactor harvest storage tank, the cells and cellular debris removed by filtration, and concentrated 10- to 100-fold by ultrafiltration through a 50 kDa or 100 kDa molecular weight cutoff ultrafiltration membrane (Millipore Corp., Bedford, Mass.). The concentrated conditioned medium was dispensed into plastic bottles and stored at or below −70° C. until purification. Under these conditions, concentrated conditioned medium contained >900 μg/ml TP10HD.

Purification Schemes

A. Affinity Chromatography

Conditioned medium derived from the hollow fiber bioreactor was subjected to purification using a monoclonal antibody (mAb) affinity resin. Monoclonal antibody YZ1 identifies an epitope on the extracellular portion of native human CR1 (Changelian PS et al., 1985, *J Immunol* 134:1851, Wong, W. et al., 1985, J. Immunol. Methods, 82:303–313). Conjugation of this mAB to Affigel-10 according to the manufacturer's directions (BioRad Corporation, Richmond, Calif.) yielded an affinity matrix capable of specifically isolating TP10HD from conditioned medium containing contaminates from bovine serum, as previously described (Yoon et al., supra). In brief, the conditioned tissue culture medium was incubated with the affinity matrix at 4° C., overnight with gentle mixing. This mixture was poured into a chromatography column and washed extensively with 10 mM Hepes, 0.1 M NaCl pH 7 buffer to remove all nonspecifically bound material from the matrix. The TP10HD was desorbed from the matrix with 20 mM sodium phosphate, 0.7 M NaCl, pH 12 buffer and the column fractions examined for the presence of protein using a commercially available assay (BioRad Corporation, Richmond, Calif.). Fractions containing protein were pooled and dialyzed at 4° C., against phosphate buffered saline, pH 7.2–7.4. Presence of TP10HD in the preparation was confirmed with a TP10HD specific immunoassay. This procedure yielded a preparation of TP10HD estimated to be >90% pure by 4–20% linear gradient SDS-PAGE.

B. Combination Chromatography

Conditioned tissue culture medium from roller bottle cultures or the fluidized bed perfusion bioreactor cultures was processed through a series of chromatographic steps. The conditioned medium was acidified with 1N HCl and the pH lowered to 5.2–5.5. During acidification the medium became cloudy and was subsequently clarified by filtration through 0.45 and 0.2 μm membranes. The acidified, clarified conditioned medium was applied to a cation exchange column, S-Sepharose (Pharmacia Fine Chemicals, Piscataway, N.J.) equilibrated in sodium phosphate, 0.02M, sodium chloride, 0.06M, pH 5.5, buffer. Following application of the sample, washing of the column was continued with the starting buffer until the absorbance had returned to baseline. Under these conditions all TP10HD glycoforms bound to the resin while the majority of the contaminating proteins from the tissue culture medium remain unbound and passed through the column. TP10HD was eluted from the column with sodium phosphate, 0.02M, sodium chloride, 0.50M, pH 8.0, buffer. Elution of the TP10HD-containing pool was monitored by absorbance at 280 nm.

The S-Sepharose eluate was mixed with ammonium sulfate to a final concentration of 0.8–0.9 M and applied to a hydrophobic interaction column, Butyl-Sepharose (Pharmacia Fine Chemicals, Piscataway, N.J.) equilibrated with sodium phosphate, 0.1 M, ammonium sulfate, 0.9 M, pH 7.0 buffer. Following application of the sample, washing of the column was continued with the starting buffer until the absorbance had returned to baseline. Under these conditions all TP10HD glycoforms bound to the resin while contaminating proteins remained unbound and passed through the column. TP10HD was eluted from the column with sodium phosphate, 0.1 M, pH 7.0 buffer; the removal of ammonium sulfate from the eluting buffer causes desorption of the TP10HD from the resin. Elution of the TP10HD containing pool was monitored by absorbance at 280 nm.

The butyl-Sepharose eluate was applied to a size exclusion column, Sephacryl S-300 (Pharmacia Fine Chemicals, Piscataway, N.J.) equilibrated with phosphate buffered saline (0.01 M sodium phosphate, 0.15 M sodium chloride), pH 7.2–7.4. Following application of the sample elution of the TP10HD was monitored by absorbance. Material eluting just after the exclusion volume of the column was collected and the quantity of purified TP10HD determined with an enzyme immunoassay specific for TP10HD. Aliquots were stored frozen at or below −700° C. This protocol yielded a preparation of TP10HD estimated to be >90% pure by 4–20% linear gradient SDS-PAGE.

Conclusions

Recombinant CHO DUX B11 cells expressing a modified sCR1 DNA and producing a sCR1 protein referred to as TP10HD may be cultured under laboratory conditions, for example, using hollow fiber bioreactor or roller bottles, or under large-scale culture conditions, for example, in a fluidized bed perfusion bioreactor, to yield a conditioned tissue culture medium containing secreted TP10HD. The secreted recombinant protein may be isolated by several protocols, specifically affinity chromatography, cation exchange HPLC, or a combination of ion-exchange, hydrophobic interaction, and size exclusion chromatographies, to yield a purified preparation.

EXAMPLE II

Identification of the Molecular Differences Characteristic of the TP10HD Preparations TP10HD preparations produced under different conditions and purified by multiple procedures comprise a polypeptide backbone that is glycosylated to varying extents.

Procedure

When examined by 4–20% SDS-PAGE the TP10HD preparations isolated by cation exchange HPLC and by combination chromatography as described in Example I were found to exhibit different apparent molecular weights. The material prepared by cation exchange HPLC had a lower molecular weight, approximately 30 kDa, than the material prepared by the chromatographic methodology. When each preparation was deglycosylated by n-glycanase digestion as described by the manufacturer (Genzyme Corporation, Boston, Mass.; see Example VI below), the molecular weights were reduced to a value equivalent to the theoretical molecular weight contribution of the polypeptide chain to the TP10HD molecule, approximately 200 kDa.

Conclusions

These results demonstrated that the TP10HD molecules produced under differing cell culture conditions and isolated by multiple purification strategies were composed of similar polypeptide chains glycosylated to variable levels resulting in observable differences in molecular weight. This served as the first indication that different glycoforms of TP10HD, having different carbohydrate compositions, existed.

EXAMPLE III

Further Demonstration of the Existence of TP10HD Glycoforms

HPLC analysis showed that TP10HD was composed of a mixture of glycoforms when produced from conditioned cell culture medium under one of several different sets of conditions, including (a) in a hollow fiber bioreactor; (b) in roller bottles containing microcarriers; or (c) in a fluidized bed perfusion bioreactor; and when purified either by a combination of cation exchange, hydrophobic interaction and size exclusion chromatographies, or by affinity chromatography.

Analytical Methods

Figure 1B:
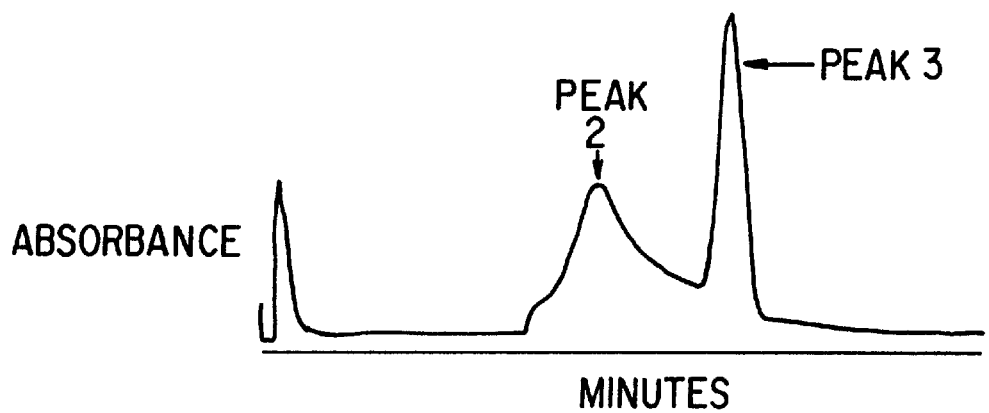
Figure 1C:
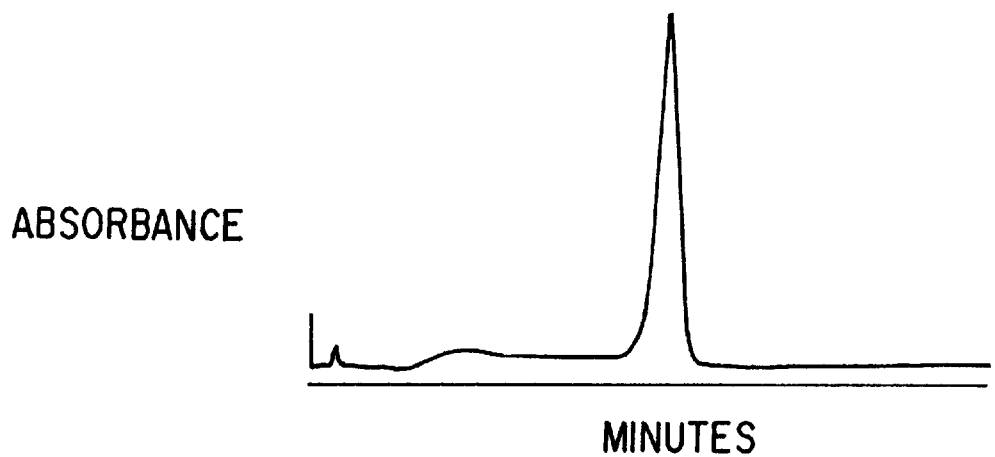

Samples of TP10HD purified by several different schemes were dialyzed against sodium phosphate, 20 mM, sodium chloride, 30 mM, pH 7.0 buffer and filtered through a 0.2 $\mu$m membrane. A Hydropore-SCX HPLC column, 10×100 mm (Rainin Instrument Company, Emeryville, Calif.), was equilibrated with the same buffer, samples applied at 2 ml/min and washing of the column was continued with the starting buffer until the absorbance returned to baseline. The NaCl concentration in the buffer was increased to 50 mM, and the TP10HD glycoform defined as weakly cationic eluted from the resin. After the absorbance returned to baseline, the highly cationic glycoform was eluted with a linear NaCl gradient, 50 to 250 mM. The results are shown in FIGS. 1A–1C.

Under these conditions of application, all glycoforms of TP10HD bound to the resin. The unabsorbed material passing directly through the column was shown to be a nonprotein, non-TP10HD contaminant, most probably cellular DNA, based on the following criteria: (a) it absorbed light in the ultraviolet spectrum; (b) it was not reactive in chemical assays for the detection of protein; (c) it was not reactive with protein- specific stains used to visualize materials on SDS-PAGE; and (d) it was not reactive in a TP10HD-specific immunoassay.

After application, the NaCl concentration in the buffer was increased to 50 mM, the TP10HD molecules defined as weakly cationic glycoforms were eluted from the resin. All of the material eluting as the weakly cationic glycoform was identifiable as TP10HD in a specific immunoassay. Finally, more tightly bound proteins were eluted from the resin by increasing the concentration of NaCl in a linear manner. At an NaCl concentration of ~125 mM, the TP10HD molecules defined as the strongly cationic glycoforms were eluted (FIGS. 1A–1C). All of the material eluting as the strongly cationic glycoform was identifiable as TP10HD in a specific immunoassay.

TP10HD Purified by Affinity Chromatography

TP10HD material purified by affinity chromatography contained multiple glycoforms when analyzed by the HPLC cation exchange procedure. The absorbance trace shown in FIG. 1A demonstrates that the predominant glycoforms were strongly cationic (i.e. eluting at about 125 mM NaCl).

TP10HD Purified by Combination Chromatography

When analyzed by the HPLC cation exchange procedure, the material derived from the fluidized bed perfusion bioreactor was shown to contain multiple glycoforms of TP10HD. The ratios of concentration of weakly cationic glycoforms to strongly cationic glycoforms ranged from 70:30 to 80:20 (FIG. 1B). Material derived from the roller bottle cultures was also shown to contain multiple glycoforms of TP10HD, with the ratio of weakly cationic glycoforms to strongly cationic glycoforms being 76:24.

TP10HD Purified by HPLC Cation Exchange Chromatography

This material was shown to contain only the strongly cationic glycoform of TP10HD (FIG. 1C). As previously disclosed (International Patent Pub. WO89/09220 and WO91/05047; Weisman H F et al., 1990. *Science* 249:146; Yeh C G et al., 1991, *J Immunol* 146:250), the material isolated in this way demonstrated the in vitro and in vivo functional characteristics of human sCR1 protein.

Conclusions

These results demonstrated that multiple TP10HD glycoforms, distinguishable by cation exchange chromatography, exist in conditioned medium derived from fluidized bed perfusion bioreactors, roller bottle cultures, and hollow fiber bioreactor derived conditioned medium, although the proportions of the different glycoforms in the different source media may vary significantly.

EXAMPLE IV

Isolation of Purified Preparations of the Weakly and Strongly Cationic Glycoforms Preparations of weakly and strongly cationic glycoforms can be prepared by HPLC.

Methods

Preparative HPLC was carried out on a 21.4 mm×100 mm sulfopropyl substituted ion exchange resin column (Hydropore-SCX, Rainin Instrument Company, Inc., Emeryville, Calif.). The column was equilibrated in 20 mM sodium phosphate, 30 mM NaCl, pH 7.0 buffer. A sample of TP10HD purified by combination chromatography as described above was dialyzed against the same buffer prior to use. Following application of the sample, development of the column was continued, typically for 20 minutes, with the same buffer to wash nonspecifically bound proteins from the resin. The buffer was changed to 20 mM sodium phosphate, 50 mM NaCl, pH 7.0, and development continued, typically for an additional 20 minutes, until all of the weakly cationic glycoform had eluted from the column. Finally the development of the column was completed with a linear, 50–250 mM NaCl gradient (20 mM sodium phosphate, pH 7.0 buffer). The strongly cationic glycoform typically eluted from the column with ~125 mM NaCl.

Results

In a typical preparation, a 125 ml sample, containing approximately 100 mg of TP10HD, was applied to the column. The fractions corresponding to the weakly (TP10HD-CCW) and strongly (TP10HD-CCS) cationic glycoforms were pooled as indicated and the quantity of TP10HD determined with a TP10HD specific immunoassay.

Conclusions

Sufficient quantities of the multiple glycoforms of TP10HD were isolated to permit in vitro and in vivo functional studies and detailed biochemical analyses.

EXAMPLE V

Resolution of TP10HD Glycoforms by Cation Exchange Chromatography with S-Sepharose after TP10HD Purification The HPLC cation-exchange purification protocol described above resolved glycoforms of TP10HD into two fractions (see, for example, FIG. 1B), a peak referred to as "peak 2" (more heavily glycosylated material) which is the second peak from the left, and "peak 3" (less heavily glycosylated material) which is the rightmost peak. The initial protocol was developed using a HPLC cation exchange column, Hydropore-SCX, purchased from Rainin Instruments. It was observed that over a prolonged period of time, the results of this chromatographic step became variable. This inconsistency was attributed to a limitation in the usable life of this HPLC column under the conditions of its use and storage.

The present inventors therefore sought an alternative purification method for resolving sCR1 glycoforms that was more consistently reproducible over time. Rather than evaluate HPLC columns available from various other suppliers, a conventional cation exchange resin, S-Sepharose Fast Flow resin (Pharmacia) was selected for testing. This resin was chosen primarily because the functional group on S-Sepharose is the same as the functional group of the Hydropore-SCX column described above. The only difference between these resins is in the support matrix: agarose (S-Sepharose) versus a silica-based packing covered with a hydrophilic polymer layer (SCX).

A 2.5 cm Kontes-Flex column was prepared with S-Sepharose having packed dimensions of 2.5×1.8 cm, and an in-line UA-6 UV monitor (Isco).

The TP10HD material tested in this study was produced using the fluidized bed perfusion bioreactor (Verax System S200; see above), and had a protein concentration of 5.5 mg/ml. The TP10HD material obtained from the concentrated conditioned cell culture medium had been subjected first-to a series of purification steps prior the present study (see commonly assigned U.S. Patent Application, Gail Folena-Wasserman et al., for "Protein Purification," filed Mar. 24, 1992, Ser. No. 07/857,022, which is hereby incorporated by reference in its entirety).

First, the crude medium was subjected to cationic exchange chromatography on S-Sepharose and eluted with 20 mM sodium phosphate, 500 mM NaCl, pH 7.0. The eluted protein was precipitated with ammonium sulfate, resolubilized, and adsorbed onto a hydrophobic interaction chromatographic support, a butyl-TOYOPEARL column, equilibrated with 0.8M $(NH_4)_2SO_4$ in 100mM sodium phosphate, pH 7.0. The desired material was eluted with 0.7 M $(NH_4)_2SO_4$ in 100 mM sodium phosphate, pH 7.0. The eluate was adsorbed onto an anionic exchange support, DEAE-TOYOPEARL, eluted, and subjected to a second cationic exchange chromatography step employing as a support TOYOPEARL CM 650S. The protein was eluted with a 5 column volume linear gradient of 0–250 mM NaCl in 50 mM MES/MES.Na, pH 5.5 and neutralized with 1/10 volume of 0.5 M dibasic Na phosphate. The TOYOPEARL CM product was then subjected to size exclusion chromatography on a column of TOYOPEARL HW65S, previously equilibrated with 10 mM sodium phosphate, 0.9% w/v NaCl, pH7. The entire product peak was collected and concentrated for storage. The TP10HD material was now ready for testing in the present study.

The following buffers were used for the S-Sepharose fractionation: Equilibration and Wash Buffer—20 mM Na phosphate, 30 mM NaCl, pH 5.2; Wash 2 Buffer and Buffer A—20 mM Na phosphate, 50 mM NaCl, pH 7.0; Buffer B—20 mM Na phosphate, 250 mM NaCl, pH 7.0.

A sample of 1.5 ml of purified TP10HD (8.25 mg protein) was applied to the S-Sepharose column previously equilibrated to pH 5.2. The column was then washed until the effluent gave baseline readings ($A_{280}$). The column was then washed with 2.5 bed volumes of Wash Buffer 2. A linear gradient (10 bed volumes) of buffer A and buffer B (50 to 250 mM NaCl) was applied. The eluted TP10HD fraction was collected as a single pool on the basis of UV absorbance. The protein concentration of each fraction was determined by A280 using an extinction coefficient for a 1% solution E (1%/280) equal to 10 cm$^{-1}$.

Results

Figure 2:
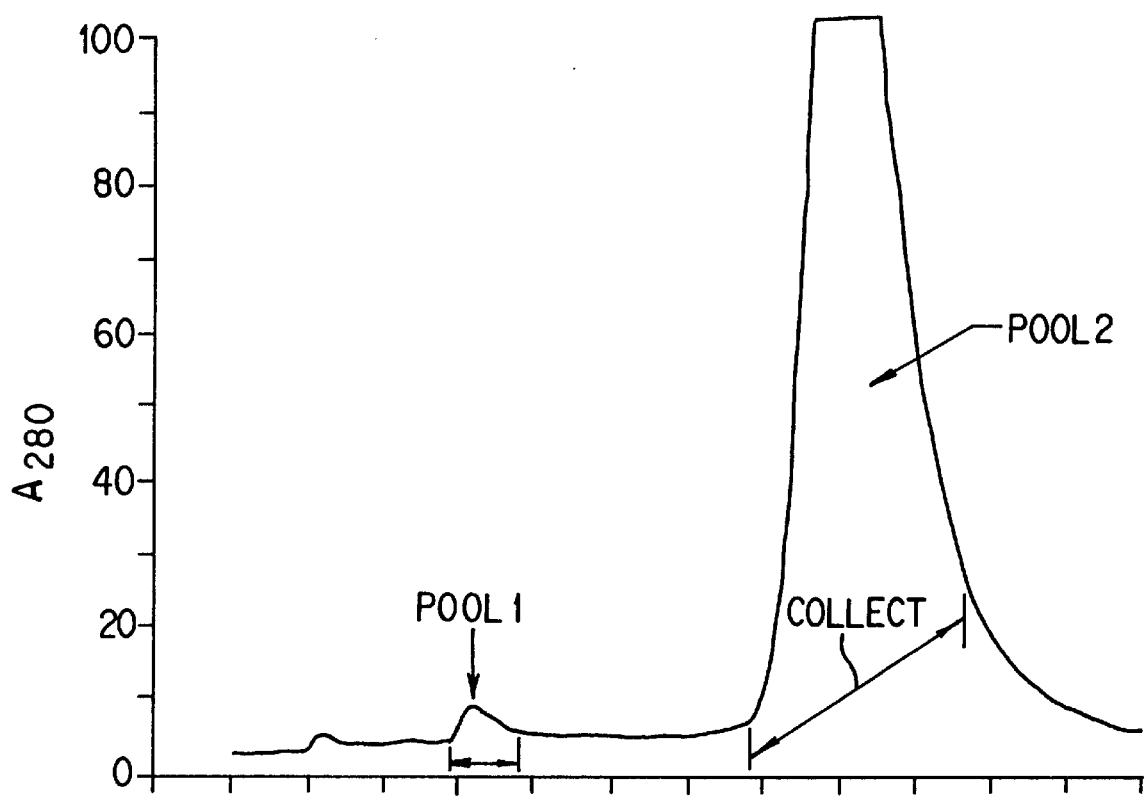
FIG. 2 shows an elution profile of TP10HD from an S-Sepharose column with a 50–250 mM NaCl gradient. Peaks corresponding to Pool 1 and Pool 2 are indicated. The flow rate was 2 ml/min. The chart speed was 0.25 cm/min. The sensitivity was 0.2 absorbance units at 280 nm full scale.
Figure 4A:
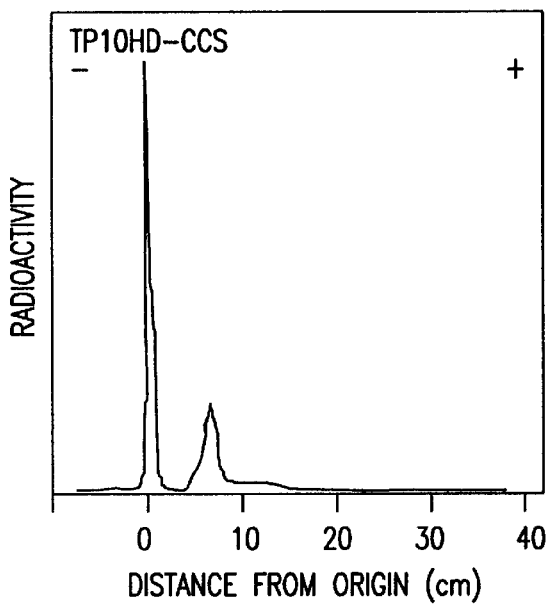
FIGS. 4A–4D show four radioelectrophoretograms of oligosaccharide chains from TP10HD-CCW (FIGS. 4A, 4C) and TP10HD-CCS (left panels).
Figure 4B:
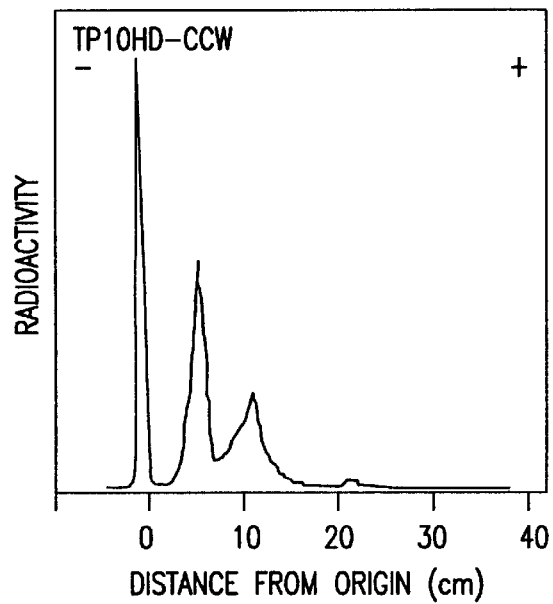
Figure 4C:
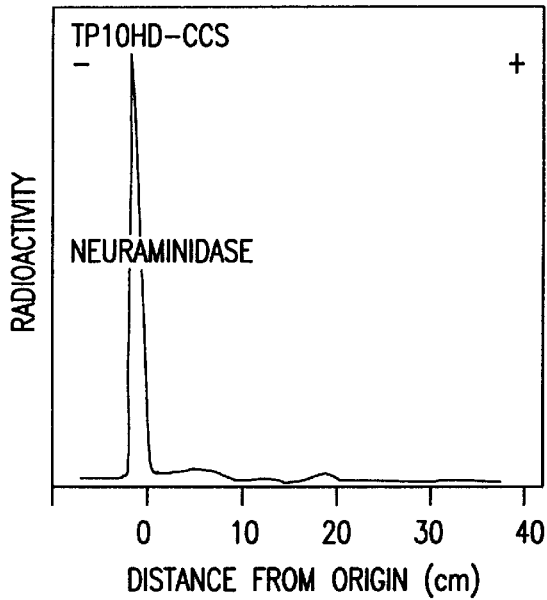
Figure 4D:
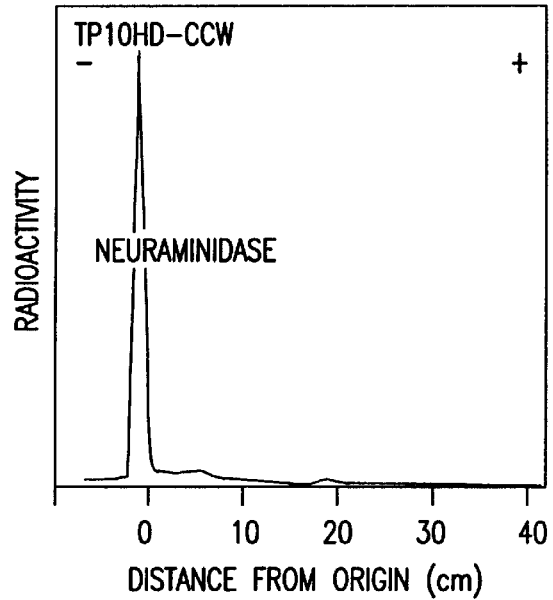

The results are shown in FIGS. 2 and 3. The minor peak shown in FIG. 2, termed Pool 1, corresponding to "peak 2" in FIG. 1B, represented 2% of the applied sample. The major peak in FIG. 2, termed Pool 2 (corresponding to "peak 3" in FIG. 1B) represented about 89% of the applied sample.

SDS PAGE was performed on the above two pools. The results are shown in FIG. 3. The material in Pool 1 had a higher molecular weight upon SDS-PAGE than did the material in pool 2.

Conclusion

Based on the above results, it was concluded that a non-HPLC cation-exchange chromatographic method, using S-Sepharose, was a useful means for reproducibly separating two major glycoform fractions of TP10HD, and was preferred to the HPLC SCX column method described above. This purification step could be performed, as here, after a multistep purification of TP10HD from conditioned medium. Alternatively, the initial S-Sepharose step in the multistep purification process could be used to separate the different glycoforms, and the further purification of these glycoforms performed independently.

EXAMPLE VI

Pharmacokinetic Studies of sCR1 Glycoforms

Plasma pharmacokinetic half-lives and/or clearance rates of different glycoform preparations were determined. The weakly cationic glycoform exhibited increased plasma half-life and/or lower total clearance rates compared to the strongly cationic glycoform and both glycoforms exhibited significantly greater plasma half-lives and/or lower total clearance rates than enzymatically deglycosylated glycoform preparations.

Materials and Methods

A. Sources of Study Material

See the Definition Section, above, for a definition of the various TP10HD preparations (TP10HD-CX, TP10HD-CC, TP10HD-CCW, TP10HD-CCS, and TP10HD-CXD). Test material was purified as described in Example I.

B. Pharmacokinetic Studies

Nine different pharmacokinetic studies are listed in Table 2, below.

TABLE 2

| STUDY # | MATERIAL | ANIMAL SPECIES |
| --- | --- | --- |
| 1 | TP10HD-CX | rats |
| 2 | TP10HD-CX | rabbits |
| 3 | TP10HD-CC | pigs |
| 4 | TP10HD-CC | rats |
| 5 | TP10HD-CCW | rats |
| 6 | TP10HD-CCW | rabbits |
| 7 | TP10HD-CCS | rats |
| 8 | TP10HD-CCS | rabbits |
| 9 | TP10HD-CXD | rats |

C. Iodination of the Study Material

In Studies 1, 2, 4, 5, 7 and 9, Iodination was carried out by the chloramine-T procedure. Sodium phosphate buffer, 0.5 M, pH 7.6, 50 $\mu$l, was added to 1 mCi of Na-$^{125}$I (New England Nuclear, Boston, Mass.) as supplied. The sample of TP10HD, typically 100 $\mu$g in 100 $\mu$l (Study 5=69 $\mu$g; Study 7=34 $\mu$g; Study 9=91 $\mu$g), was added, followed by 50 $\mu$l of a 15 mg/ml solution of freshly prepared chloramine-T. The reaction mixture was vigorously shaken for 60 seconds. Sodium metabisulfite (50 $\mu$l, 15 mg/ml) and sodium iodide (100 $\mu$l, 10 mg/ml) were successively pipetted into the reaction vial. The reaction mixture was passed onto a PD10 column (Pharmacia Fine Chemicals, Piscataway, N.J.), pre-equilibrated with phosphate buffered saline, pH 7.2–7.4, containing 0.1% bovine serum albumin (sigma Chemical Company, St. Louis, Mo.). Ten 0.5 ml fractions were collected and 2 $\mu$l aliquots were counted directly and after combining with 100 $\mu$l of a 0.1% bovine serum albumin solution and 1 ml of 20% trichloroacetic acid. After incubation at 0° C. for 1 hour, the acid-precipitable protein associated radioactivity was collected by centrifugation for 10 minutes at 1000×g and quantitated by scintillation counting. Fractions containing >90% of the total radioactivity in the acid precipitate were pooled for further use.

In Studies 6 and 8, iodination was performed by the iodogen method (Fraker et al., 1978, *Biochem Biophys Res Commun* 80:849); the average degree of $^{125}$I substitution was 0.56 atoms/molecule of protein resulting in a specific activity of 22.7 kBq/mg for STUDY 6, and the average degrees of $^{125}$I substitution was 0.76 atoms/molecule of protein resulting in a specific activity of 29.5 kBq/mg for STUDY 8.

D. Preparation of Dosing Solution

Study 1: Radioiodinated TP10HD-CX was mixed with purified unlabeled TP10HD-CX to yield a dosing solution suitable for administering a 1 mg/kg total TP10HD dose containing 16–25×10$^6$ cpm of radiolabeled TP10HD-CX.

Study 2: Radioiodinated TP10HD-CX, ~5% w/w, was mixed with purified TP10HD-CX to yield a dosing solution containing 1 mg/ml TP10HD-CX in 0.1 M Hepes, 0.15 M NaCl, pH 7.4 buffer.

Study 3: TP10HD-CC was administered as supplied to a final dose of 1 mg/kg.

Study 4: Radioiodinated TP10HD-CC was mixed with purified unlabeled TP10HD-CC to yield a dosing solution suitable for administering a 1 mg/kg or a 3 mg/kg total TP10HD dose containing ~20×10$^6$ cpm.

Study 5: Radioiodinated TP10HD-CCW was mixed with purified unlabeled TP10HD-CCW to yield a dosing solution suitable for administering a 1 mg/kg total TP10HD dose containing ~20×10$^6$ cpm.

Studies 6 and 8: As described in STUDY 2 except that the radioiodinated TP10HD-CCW was added to ~1% w/w.

Study 7: Radiolabeled TP10HD-CCS was mixed with purified unlabeled TP10HD-CCS to yield a dosing solution suitable for administering a 1 mg/kg total TP10HD dose containing ~20×10$^6$ cpm.

Study 9: Radioiodinated TP10HD-CXD was mixed with purified unlabeled TP10HD-CXD to yield a dosing solution suitable for administering a 1 mg/kg total TP10HD dose containing ~20×10$^6$ cpm.

E. Protocols

In Studies 1, 4, 5, 7 and 9, test material was injected intravenously (iv) into four Sprague-Dawley rats (2 male, 2 female). Blood samples were obtained from the retroorbital plexus at 1, 3, 5, 10, 20, 30, 45, and 60 minutes post injection, and the radioactivity determined. Additional post infusion blood samples were taken at 2, 3, and 4 hours postinjection (STUDY 4) and at 120 minutes (STUDY 5). The plasma fraction of the remaining blood sample was retained for further analysis.

Plasma samples were analyzed for residual test material by measuring:

(1) total residual radioactivity;
(2) percentage of radiolabeled material precipitated with TCA;
(3) residual acid precipitable radioactivity in the presence of SDS; and
(4) material immunologically identifiable in an enzyme immunoassay as TP10HD.

Radioisotope data was quantitated as total cpm/ml blood or plasma and as the percentage of a theoretical time zero value. Pharmacokinetic half-life was calculated from the radiometric data.

In Study 2, test material was injected iv into two groups of five male Dutch rabbits (approximately 1 kg) at a dose of 1 mg/kg. Blood samples, 2 ml, were taken from an ear artery immediately pre-dosing and at 5, 10, 20, 45, 60, 120, and 180 minutes, and mixed with heparin (final concentration 25 $\mu$g/ml). Radioactivity was determined in an aliquot by scintillation counting, and the plasma, obtained by centrifugation at 2000×g for 5 minutes, was stored at −40° C.

Plasma samples were analyzed for residual test material by an in vitro functional assay, inhibition of hemolysis of antibody coated sheep red blood cells (SRBC) by human complement. Pharmacokinetic half-life was calculated from the titer of the residual functional activity.

In Study 3, test material was injected iv through a jugular vein cannula into piglets ranging in weight from 4.5 to 6.1 kg. Blood samples were taken via a previously implanted jugular vein cannula into syringes containing lithium heparin at a final concentration of 15 units/ml. A preinfusion sample, 10 ml, was taken at zero time and postinfusion samples, 1.0 ml, were taken at 5, 10, 15, 30, 45, 60, 120, 180, 240, 300, 360 minutes and 24 hours. Anticoagulated blood samples were centrifuged at ~3000 rpm, 4° C., 5 minutes and the platelet-poor plasma was aliquotted and stored at or below −70° C.

Plasma samples were analyzed for residual test material by an in vitro functional assay, as above, using pig rather than human complement. Pharmacokinetic half-life was calculated from the titer of the residual functional activity.

In Studies 6 and 8, test material was injected iv into a group of 5 Dutch rabbits (approximately 1 kg) at a dose of 1 mg/kg. Blood samples, 1 ml, were taken from an ear artery immediately predosing and at 5, 10, 20, 30, 60, 120 and 180 minutes, mixed with heparin, and radioactivity determined in an aliquot by scintillation counting after precipitation with trichloroacetic acid.

Plasma samples were analyzed for residual test material by an enzyme immunoassay (EIA) specific for TP10HD. Pharmacokinetic half-life was calculated from both the radiometric and immunoassay data.

F. N-glycanase treatment

In Study 9, removal of N-linked oligosaccharide chains was performed by n-glycanase digestion, performed according to manufacturer's instructions (Genzyme Corporation, Boston, Mass.). Typically, 58 $\mu$g TP10HD-CX was incubated with 10.5 units of n-glycanase for 18 hours, 37° C., in 0.2M sodium phosphate, pH 8.6 buffer.

G Acid precipitation

Precipitation with trichloroacetic acid was performed as follows: Plasma (20 $\mu$l) was precipitated by sequential addition of 450 $\mu$l of 0.13 M Tris HCl, 4% SDS, 10% glycerol, pH 6.8 buffer, followed by 30 $\mu$l of fetal bovine serum and 500 $\mu$l of 20% trichloroacetic acid. After each addition, the tubes were vigorously mixed and incubated for 72 hours at 4° C.; the pellets of precipitable protein were collected by centrifugation at 1000×g for 10 minutes, the supernatants removed and discarded, and the residual radioactivity measured by scintillation counting.

H. Enzyme Immunoassay

A commercially available assay was utilized (Cellfree® CD35, T Cell Diagnostics, Inc. Cambridge, Mass.). In brief, polystyrene beads coated with polyclonal rabbit anti-TP10HD antibodies were simultaneously incubated with the diluted test sample and a horse radish peroxidase-conjugated polyclonal rabbit anti-TP10HD antibody. Following incubation, the beads were removed from the reaction mixture, washed of nonspecifically bound material, and subsequently incubated in the presence of an appropriate dilution of substrate. Color development was terminated by the addition of sulfuric acid and the absorbance (optical density) determined as a measure of TP10HD concentration.

I. Hemolysis Assay

Rabbit plasma samples were heated at 56° C. for 1 hour in the presence of methylamine (12.5 mM) in order to amidate thioester groups and to inactivate endogenous complement components C3 and C4. This procedure eliminated endogenous rabbit complement activity in the test samples without significantly affecting the activity of TP10HD. Test samples were then diluted 1:50 with 0.1 Hepes, 0.15 M NaCl, pH 7.4 buffer and assayed.

SRBC presensitized with rabbit anti-SRBC antibody (Diamedix, Miami, Fla.) were mixed in a V-bottom microtiter wells (Costar, Cambridge, Mass.) with an appropriate dilution of the test plasma and an aliquot of diluted human serum as a complement source. After incubation, 37° C., 1 hour, the unlysed red cells were pelleted by centrifugation, the supernatant transferred to corresponding flat bottom microwells (Costar, Cambridge, Mass.), and absorbance at 415 nm measured. Inhibition of complement-mediated lysis of the antibody coated SRBC was measured as a reduction in the absorbance in the presence of test sample. Standard curves with known quantities of TP10HD can be used to calibrate the assay so that results can be expressed as mg/ml TP10HD remaining in the plasma versus time.

Study 3 Hemolytic Assay

Prior to infusion with TP10HD-CC, plasma was collected from each pig to be used as a sample diluent and complement source for the hemolysis assay. Test samples were diluted a minimum of 1:50 with 0.1 M Hepes, 0.15 M NaCl, pH 7.4 buffer. For greater dilution, test samples were diluted with preinfusion plasma already diluted 1:50 in the same buffer, thereby maintaining the final plasma concentration at 1:50. At this dilution, the degree of hemolysis was equivalent to hemolysis with human complement, as described above. Other manipulations were as described above. Standard curves with known quantities of TP10HD can be used to calibrate the assay so that results can be expressed as $\mu$g/ml TP10HD remaining in the plasma versus time.

Results

The results of the pharmacokinetic studies are presented in Tables 3–7. For studies 1, 4, 5, 7, and 9, in rats, the clearances from blood of $^{125}$I-TP10HD-CX, $^{125}$I-TP10HD-CC, $^{125}$I-TP10HD-CCW, $^{125}$I-TP10HD-CCS, and $^{125}$I-TP10HD-CXD, respectively, were determined. Whole blood (~300 $\mu$l) was collected from the retroorbital plexus of each rat. Duplicate 100 $\mu$l samples from each time point were counted, averaged by group, and normalized to cpm/ml. Samples from each time point were precipitated with TCA in the presence of SDS, counted, averaged by group, and normalized to cpm/ml. Clearance was determined by total TCA-precipitable counts of $^{125}$I-labelled material and by EIA. The results, shown in Table 3, indicate a biphasic clearance pattern in each study with a short α phase half-life and a longer β phase half-life.

TABLE 3

Biphasic Clearance Profiles

| STUDY # | ANIMALS | MATERIAL | α PHASE (min) | β PHASE (min) |
|---|---|---|---|---|
| 1 | Rats | TP10HD-CX | 4.3 | 167 |
| 2 | Rabbits | TP10HD-CX | 9–11 | |
| 3 | Pigs | TP10HD-CC | 8.3 | 360 |
| 4 | Rats | TP10HD-CC | | |
| | | (1 mg/kg) | 9.2 | 181.1 |
| | | (3 mg/kg) | 9.8 | 267.1 |
| 5 | Rats | TP10HD-CCW | 12.21 | 100 |
| 6 | Rabbits | TP10HD-CCW | 8 | 216 |
| 7 | Rats | TP10HD-CCS | 6.64 | 133 |
| 8 | Rabbits | TP10HD-CCS | 6 | 216 |
| 9 | Rats | TP10HD-CXD | <1 | 6.1 |

TABLE 4

Serum Pharmacokinetics of TP10HD-CX in Rabbits (STUDY 2)

| Measure | Units | Group 1 | Group 2 |
|---|---|---|---|
| Serum half-life | min | 9.1 ± 1.4 | 11.1 ± 1.2 |
| Volume of Distribution | ml/kg | 67.0 ± 9.0 | 44.6 ± 3.7 |
| Peak (t = O) conc | μg/ml | 16.5 ± 2.4 | 23.7 ± 1.7 |
| Total Clearance | ml/min/kg | 5.8 ± 1.2 | 2.9 ± 0.1 |

TABLE 5

Serum Pharmacokinetics of TP10HD-CC in Pigs (STUDY 3)

| Measure | Units | Mean (8 animals) |
|---|---|---|
| Serum half-life, α-phase | min | 8.3 |
| Serum half-life, β-phase | min | 363 |
| Volume of Distribution, α-phase | ml/kg | 36 |
| Volume of Distribution, β-phase | ml/kg | 73 |
| Peak (t = O) concentration | μg/ml | 29.3 |
| Total Clearance | ml/min/kg | 0.24 |

Plasma samples taken 24 hours after dosing gave levels of TP10HD-CC which were not distinguishable from control levels. The pharmacokinetic parameters for clearance rate, compartment volume, rate constants and half-life were obtained by fitting the data for each pig to two and three compartment models. Statistical analysis showed that, for some pigs, a three-compartment model was a better fit whereas, for other pigs, a two-compartment model was better; to avoid complexity data for all the pigs, the data was processed using a two-compartment model. The mean half-life was found to be 8.3 minutes for the α-phase and 6 hours for the β-phase. These phases represent 69% and 31% respectively of the given dose such that approximately one-third of the dose was cleared slowly.

This study demonstrated that the TP10HD-CC preparation showed a marked biphasic clearance pattern in which the β-phase was very much slower than the α-phase. These results are consistent with differential clearance of glycoform populations, with some species being very slowly removed.

The results of Study 6 are summarized in Table 6, below.

TABLE 6

Serum Pharmacokinetics of TP10HD-CCW in Rabbits (Study 6)

| Measure | Units | Radiometric Data | Immunoassay Data |
|---|---|---|---|
| Serum half-life, α-phase | min | 7.8 ± 0.5 | 14 |
| % dose cleared, α-phase | | 30.9 ± 1.5 | 30 |
| Serum half-life, β-phase | min | 216.6 ± 18.8 | 376 |
| % dose cleared, β-phase | | 69.1 ± 1.9 | 70 |
| Volume of Distribution, α-phase | ml/kg | 56.2 ± 1.0 | |
| Volume of Distribution, β-phase | ml/kg | 22.6 ± 1.9 | |
| Peak (t = O) concentration | μg/ml | 17.8 ± 0.3 | |
| Total Clearance | ml/min/kg | 0.26 ± 0.02 | 0.1 |

The pharmacokinetic half-life of TP10HD-CCW as determined by radiometric analysis was approximately 8 minutes for the α-phase and 216 minutes for the β-phase. Approximately 30% of the total dose was cleared during the rapid α-phase and 70% of the total dose was cleared during the longer β-phase. The total clearance rate for this glycoform was 0.26 ml/min/kg and the compartment volume for the β-phase was ~23 ml/kg.

The results of Study 8 are summarized in Table 7, below.

TABLE 7

Serum Pharmacokinetics of TP10HD-CCS in Rabbits (Study 8)

| Measure | Units | Radiometric Data | Immunoassay Data |
|---|---|---|---|
| Serum half-life, α-phase | min | 6.0 ± 0.4 | 10 |
| % dose cleared, α-phase | | 74.5 ± 1.4 | 73 |
| Serum half-life, β-phase | min | 216.5 ± 36.8 | 76 |
| % dose cleared, β-phase | | 25.5 ± 1.5 | 27 |
| Volume of Distribution, β-phase | ml/kg | 69.8 ± 4.8 | |
| Volume of Distribution, β-phase | ml/kg | 162.0 ± 13.9 | |
| Peak (t = O) concentration | μg/ml | 14.6 ± 1.0 | |
| Total Clearance | ml/min/kg | 0.85 ± 0.12 | 1.24 |

The pharmacokinetic half-life of TP10HD-CCS as determined by radiometric analysis was approximately 6 minutes for the α-phase and 216 minutes for the β-phase. Approximately 75% of the total dose was cleared during the rapid α-phase and 25% of the total dose was cleared during the longer β-phase. The total clearance rate for this glycoform was 0.85 ml/min/kg and the compartment volume for the β-phase was ~162 ml/kg.

In Study 9, the pharmacokinetic half-life of TP10HD-CXD as determined by radiometric analysis was <1 minute for the α-phase and 6.1 minutes for the β-phase.

Summary

The results presented above demonstrate that purified preparations of TP10HD contain glycoforms which differ in clearance rates. The conclusion that such differences are due to variations in glycosylation is consistent with the results:

(1) deglycosylation of purified TP10HD preparations yields molecules with a common molecular weight, proving that the polypeptide chains of all TP10HD preparations are identical;

(2) deglycosylated TP10HD is cleared rapidly; and (3) TP10HD preparations characterized by larger molecular weights due to increased glycosylation (for example TP10HD Preparations CC and CCW), demonstrate longer plasma half-lives-and/or lower total clearance rates than preparations with lower molecular weights due to lower degrees of glycosylation (for example Preparations CX and CCS).

Comparison of the results of Studies 6 and 8 shows that the primary difference between preparations TP10HD-CCW and TP10HD-CCS is not in the half-lives characterizing the biphasic clearance, but in the proportion of material that is slowly cleared (a higher proportion in TP10HD-CCW).

As indicated below, detailed carbohydrate analysis illustrates that the differences between the TP10HD glycoforms is due to the extent of glycosylation, composition of the oligosaccharide chains, and identity of the terminal oligosaccharide carbohydrate residues.

EXAMPLE VII

Determination of the Terminal Oligosaccharide Residues of the Multiple Glycoforms of TP10HD Determination of terminal oligosaccharide residues of TP10HD demonstrated that the weakly cationic glycoform exhibits a higher level of sialylation.

Methods

The terminal carbohydrate structure of TP10HD preparations was evaluated. Samples of each preparation, 1 μg, were immobilized onto nitrocellulose membranes using a commercially available Dot-Blot apparatus (Bio-Rad, Richmond, Calif.). A commercially available Glycan Differentiation Kit which identifies terminal oligosaccharide residues on glycoproteins (Boehringer Mannheim Biochemicals, Indianapolis, Ind.) was used according to the manufacturer's directions. This kit contains five digoxigenin-lectin probes: *Galanthus nivalis* agglutinin (GNA); *Sambucus nigra* agglutinin (SNA); *Maackia amurensis* agglutinin (MAA); Peanut agglutinin (PNA); and *Datura stramonium* agglutinin (DSA).

In brief, replicate samples of each TP10HD preparation were probed with a digoxigenin-lectin complex; by changing the lectin the specificity of the probe is altered to allow detection of a variety of carbohydrate residues. After binding, the probes were visualized by detection of digoxigenin epitopes with an alkaline phosphatase-conjugated sheep anti-digoxigenin Fab' reagent; color development occurred within 5 minutes after addition of substrate.

The results are summarized in Table 8.

TABLE 8

Terminal Oligosaccharide Residues of the Multiple Glycoforms of TP10HD

| | LECTIN | | | | |
|---|---|---|---|---|---|
| | GNA | SNA | DSA | MAA | PNA |
| Carbohydrate specificity | terminal Man | NeuAc α(2–6) Gal | Gal β(1–4) GlcNAc | NeuAc α(2–3) Gal | Gal β(1–3) GlcNac |
| TP10HD-CX | + | – | – | – | – |
| TP10HD-CC | – | – | + | + | – |
| TP10HD-CXD | – | – | – | – | – |
| TP10HD-CCW | – | – | ± | ± | – |
| TP10HD-CCS | + | – | ± | ± | – |

Abbreviations: Gal, galactose; Man, mannose; GlcNAc, N-acetylglucosamine; NeuAc, 5-N-acetylneuraminic acid = Sialic acid TP10HD-CX was reactive only with the GNA lectin, indicating that this preparation exhibited terminal mannose residues. TP10HD-CXD was, as expected, unreactive with all of the probes, indicating that the N-glycanase treatment had removed the oligosaccharide chains. TP10HD-CCW was strongly reactive with MAA and weakly reactive with DSA, indicating terminal sialic acid α(2,3) galactose and galactose β(1,4) N-acetylglucosamine structures. TP10HD-CCS was strongly reactive with GNA, indicating a preponderance of terminal mannose residues, and weakly reactive with MAA and DSA, suggesting a cross contamination with TP10HD-CCW.

Conclusions

These results demonstrate that the purified TP10HD glycoforms present differing oligosaccharide structures with the weakly cationic glycoform, TP10HD-CCW, characterized by terminal sialic acid residues and the strongly cationic glycoform, TP10HD-CX and TP10HD-CCS, characterized by terminal mannose residues. These findings suggest that the presence of terminal sialic acid residues results in slower plasma clearance or that terminal mannose residues results in a higher level of binding of the TP10HD to cellular carbohydrate receptors leading to a more rapid plasma clearance.

EXAMPLE VIII

Determination of Oligosaccharide Carbohydrate Composition and Structure of TP10HD Determination of oligosaccharide carbohydrate composition and structure of TP10HD, prepared as described in Example II showed that the sialic acid content of the more strongly cationic TP10HD glycoform was lower than the weakly cationic glycoform. Rapid plasma clearance was associated with little or no sialic acid on the oligosaccharide chains and (by inference) accessibility of the protein to mannose or galactose receptors. Slow plasma clearance was associated with one or more terminal sialic acid residues.

Monosaccharide Composition of TP10HD Glycoforms

A. Sources of Test Material

TP10HD was isolated as described in Examples I and V, above, and resolved into the weakly cationic glycoform, TP10HD-CCW, and the strongly cationic glycoform, TP10HD-CCS.

B. Methods

Analysis was performed using the following steps:

1. Dialysis of the sample (approximately 270–280 mg) against deionized water, to remove all buffer salts, followed by lyophilization.
2. Release of intact oligosaccharide chains with anhydrous hydrazine.
3. Treatment of the intact oligosaccharide chains with anhydrous methanolic HCl to liberate individual monosaccharides as O-methyl derivative.
4. N-acetylation of any primary amino groups.
5. Derivatization to give per-O-trimethylsilyl methyl glycosides.
6. Separation of these derivatives by capillary GLC (gas—liquid chromatography) on a CP-SIL8 column.
7. Identification of individual glycoside derivatives by retention time from the GLC and mass spectroscopy, compared to known standards.
8. Quantitation of individual derivatives by FID with an internal standard (13-O-methyl-D-glucose).

C. Results

The relative molar content of each monosaccharide in the two TP10HD glycoforms are shown in Table 9, below.

TABLE 9

Relative Molar Content Of Monosaccharides
In Two TP10HD Glycoforms

| Monosaccharide | TP10HD-CCS | TP10HD-CCW |
|---|---|---|
| Fucose | 1.0* | 1.0 |
| Galactose | 3.0 | 3.4 |
| Mannose | 5.4 | 4.1 |
| N-acetylglucosamine | 8.2 | 7.5 |
| Sialic acid | 0.9 | 1.3 |
| Glucose | ND | ND |
| N-acetylgalactosamine | ND | ND |
| Xylose | ND | ND |

*Values are presented relative to Fucose (=1.0).
ND = not detected.

D. Comparison with TP10HD-CC

In order to characterize any differences in monosaccharide composition that might exist between TP10HD produced in a hollow-fiber bioreactor as previously described (TP10HD-CX), the fractionated glycoforms TP10HD-CCW and TP10HD-CCS and the unfractionated material produced in a fluidized bed bioreactor (TP10HD-CC), batches of these materials were compared using another analytic approach.

Neutral and amino-sugars were determined by high performance anion-exchange chromatography combined with pulsed amperometric detection (HPAE-PAD Carbohydrate System, Dionex Corp.). Sugars were released by hydrolysis in 20% (v/v) trifluoroacetic acid at 100° C. for 6 h. Hydrolysates were dried by lyophilization or with a Speed-Vac (Savant Instruments). Residue was dissolved in 1% sodium acetate trihydrate solution and analyzed on a HPLC-AS6 column as described by Anumula et al. (Anal. Biochem. 195:269–280 (1991). Samples were analyzed in quadruplicate.

Sialic acid was determined separately by the direct colorimetric method of Yao et al. (Anal Biochem. 179:332–335 (1989)) in triplicate samples.

The results are shown in Table 10, below.

TABLE 10

Relative Molar Content of Each Monosaccharide
In TP10HD Batches And Glycoforms

| Batch No: | TP10HD-CX | | TP10HD-CCS | TP10HD-CC | | | | TP10HD-CCW |
|---|---|---|---|---|---|---|---|---|
| | R | V | | G020 | K002 | H115 | H118 | |
| Saccharide | | | | | | | | |
| Fucose | 0.7* | 0.9 | 0.5 | 0.4 | 0.6 | 0.7 | 0.6 | 0.5 |
| Galactose | 0.9 | 1.3 | 1.6 | 1.9 | 2.1 | 2.3 | 2.2 | 2.1 |
| Mannose | 3.0 | 3.0 | 3.0 | 3.0 | 3.0 | 3.0 | 3.0 | 3.0 |
| Glucosamine | 3.5 | 4.1 | 3.5 | 3.9 | 4.3 | 4.1 | 4.0 | 4.0 |
| Sialic Acid | 0.2 | 0.4 | 0.7 | 1.7 | 1.6 | 1.3 | 1.1 | 1.6 |
| Sialic/Mannose Ratio | 0.08 | 0.15 | 0.24 | 0.56 | 0.54 | 0.42 | 0.38 | 0.53 |

*Results are presented relative to Mannose (=3)
The glucosamine content in this assay is equivalent to the N-acetylglucosamine content in the assay used above.

Conclusion

The monosaccharide composition of the glycoforms TP10HD-CCW and TP10HD-CC are typical of sialic acid terminated mono-, bi-, and triantennary complex oligosaccharides fucosylated near the N-linked protein substitution site and containing a tri-mannose core. It can be concluded that glycoform TP10HD-CCW material contains a significantly higher proportion of sialic acid and/or a lower proportion of mannose than glycoform TP10HD-CCS. Differences in galactose and (N-acetyl)-galactosamine content are probably not significant. The sialic acid/mannose ratio of TP10HD-CX indicates that this material (described by Fearon et al., supra), resembles glycoform TP10HD-CCS and is distinct from TP10HD-CCW and TP10HD-CC. The latter appears to consist mainly of the weakly cationic glycoforms in agreement with other data presented above.

The results indicate that slower plasma clearance (TP10HD-CCW) correlates with a higher sialic acid content or sialic acid/mannose ratio (>0.25). A relatively low mannose content may also reflect a higher degree of branching (i.e., more bi- and triantennary structures) in this material.

EXAMPLE IX

Charge and Size Distribution Analysis of
Oligosaccharides Released from TP10HD
Glycoforms Complex oligosaccharide was released from each glycoform sample (0.6 mg) by hydrazinolysis. The oligosaccharide chains were radiolabeled by reductive tritiation. Charged oligosaccharide was subjected to high voltage paper electrophoresis under alkaline conditions and peaks were detected and quantitated by tritium radiography. The oligosaccharide chains were treated with *Arthrobacter ureafaciens* neuraminidase to remove sialic acid and the electrophoresis was repeated.

The radiolabeled desialylated (i.e., neutral) oligosaccharide chains were subjected to size exclusion chromatography on BioGel P4, 400 mesh, 2 m×15 mm (BioRad Corporation, Richmond, Calif.), as follows. Chromatography was performed in water at 55° C. at a flow rate of 0.2 ml/min. Samples were mixed with unlabeled partial acid hydrolysate of dextran as an internal standard. The radiolabeled glycoform oligosaccharide chains were detected by an in-line flow radioisotope monitor and the oligoglucose standards were detected by an in-line differential refractometer. In the results which follow, the hydrodynamic volume of the individual oligosaccharides is expressed as apparent glucose units (gu), the values being determined by cubic spline interpolation between glucose oligomers immediately adjacent to the oligosaccharide alditol.

FIGS. 4A–4D compare radioelectrophoretograms from TP10HD-CCW and TP10HD-CCS before and after neuraminidase treatment. In both cases, neuraminidase treatment rendered all the labeled oligosaccharide chains neutral, indicating that the negative charge was entirely attributable to sialic acid.

In glycoform TP10HD-CCS, about 64% of the oligosaccharide chains were initially neutral and the remainder had a mobility corresponding to a single sialic acid unit. For the oligosaccharide chains from glycoform TP10HD-CCW, there was a much higher proportion, 69%, of acidic oligosaccharides of which 40–50% had mobilities corresponding to two or more sialic acid residues. Only about 31% of the oligosaccharide chains from glycoform TP10HD-CCW were neutral prior to neuraminidase treatment.

The sizes of desialylated glycoform oligosaccharide chains detected by a size profile analysis are shown in Table 11, below.

TABLE 11

Size Profile Analysis Of Desialylated Glycoform Oligosaccharide Chains

| TP10HD-CCW | TP10HD-CCS |
| --- | --- |
| 20.1* | 20.0 |
| 17.3 | 17.3 |
| 15.0 | 15.0 |
| 14.0 | 14.0 |
| 12.8 | 12.7 |
| 11.5 | 11.6 |
| 10.4 | 10.5 |
| 9.3 | 9.3 |
| 3.0 | 3.0 |

*Values are in glucose units (gu)

Figure 5A:
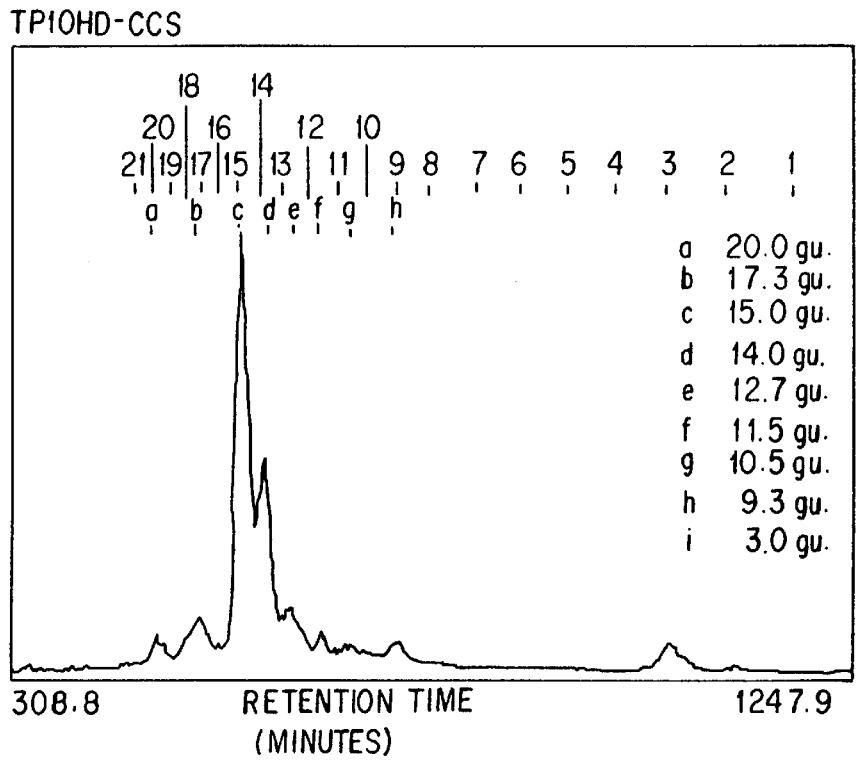
FIGS. 5A and 5B are two chromatograms showing sizes and relative proportions of oligosaccharide chains from TP10HD-CCS (FIG. 5A) and TP10HD-CCW (FIG. 5B).
Figure 5B:
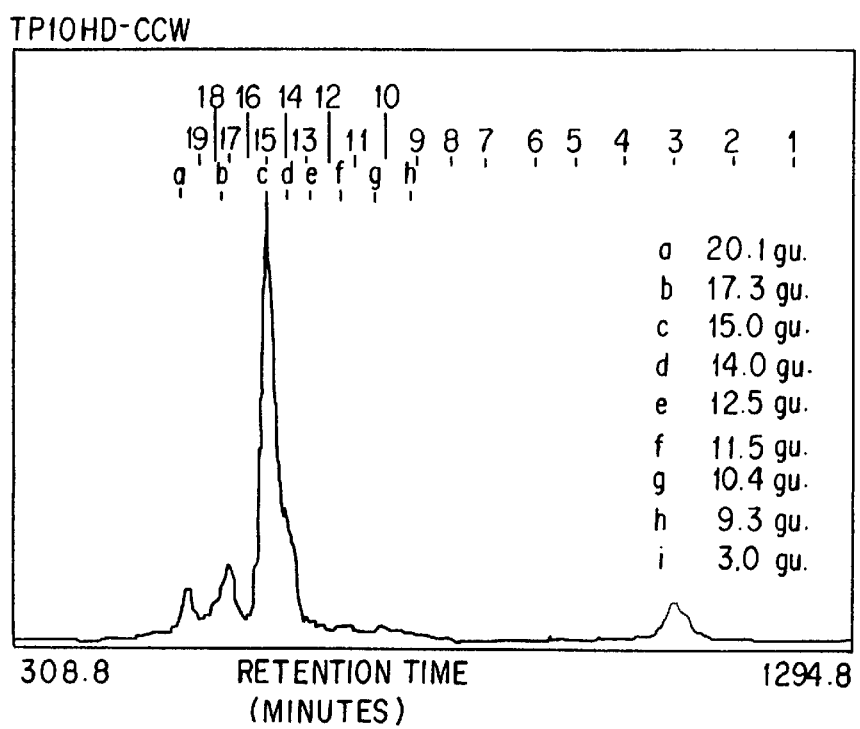

Thus, the oligosaccharide chains derived from the glycoforms were very similar in size. However, as shown in FIGS. 5A and 5B, the relative proportions of the various sizes differed. TP10HD-CCW contains a higher proportion of the larger sized oligosaccharide chains, especially the dominant 15 gu oligosaccharide, and a lower proportion of the 14 gu species, than TP10HD-CCS.

Conclusions

The charge distribution data further confirm the correlation between a high sialic acid content and slow plasma clearance demonstrated by TP10HD-CCW. The relative proportions of acidic and neutral oligosaccharide chains are similar to the proportions of the material cleared rapidly and slowly from the plasma for the two glycoforms (see Example VI). This suggests that glycoprotein molecules in which the predominant N-linked oligosaccharide chain have one or more sialic acid residues would be slowly cleared from the plasma, whereas neutral oligosaccharide chains are associated with rapid plasma clearance by an as yet unknown mechanism.

The oligosaccharide chain size profile alone does not permit unambiguous identification of the precise structures of the complex oligosaccharide chains. However, the composition and size data together are consistent with a major structure containing a trimannose core (i.e. biantennary) with variable sialylation of terminal galactose and variable fucosylation. Additional possibilities include further branching to give a triantennary structure with three Gal units. It is clear that the size profile itself does not suggest any major structural type associated with slow plasma clearance.

Slow plasma clearance correlates only with the extent of sialylation of a small number of core structures of the above type.

EXAMPLE X

The pI of the Weakly Cationic TP10HD Glycoform is Lower than the Strongly Cationic Glycoform The pI of the heavily sialylated glycoform is lower than the pI of the lightly sialylated glycoform.

Methods

Chromatofocusing is a method of separating isoforms of proteins according to their isoelectric point, pI, using an ion exchange column and a pH gradient created with amphoteric buffers of different pH. In this study, analysis of the TP10HD preparations was performed using a pH gradient of 7.1 to 4.0. The chromatographic resin was Mono P, Hr5/5 (Pharmacia Fine Chemicals, Piscataway, N.J.); the starting buffer was 0.025 M Bis/Tris titrated to pH 7.1 with saturated iminodiacetic acid; the eluant was polybuffer 7–4 (Pharmacia Fine Chemicals, Piscataway, N.J.) diluted 1:10 (v/v) with water and adjusted to pH 4.0 with HCl; cleaning buffer was 2 M NaCl in water. The experimental conditions were chosen to yield a linear pH gradient of 7.1 to 4.0 units.

Results

Figure 6:
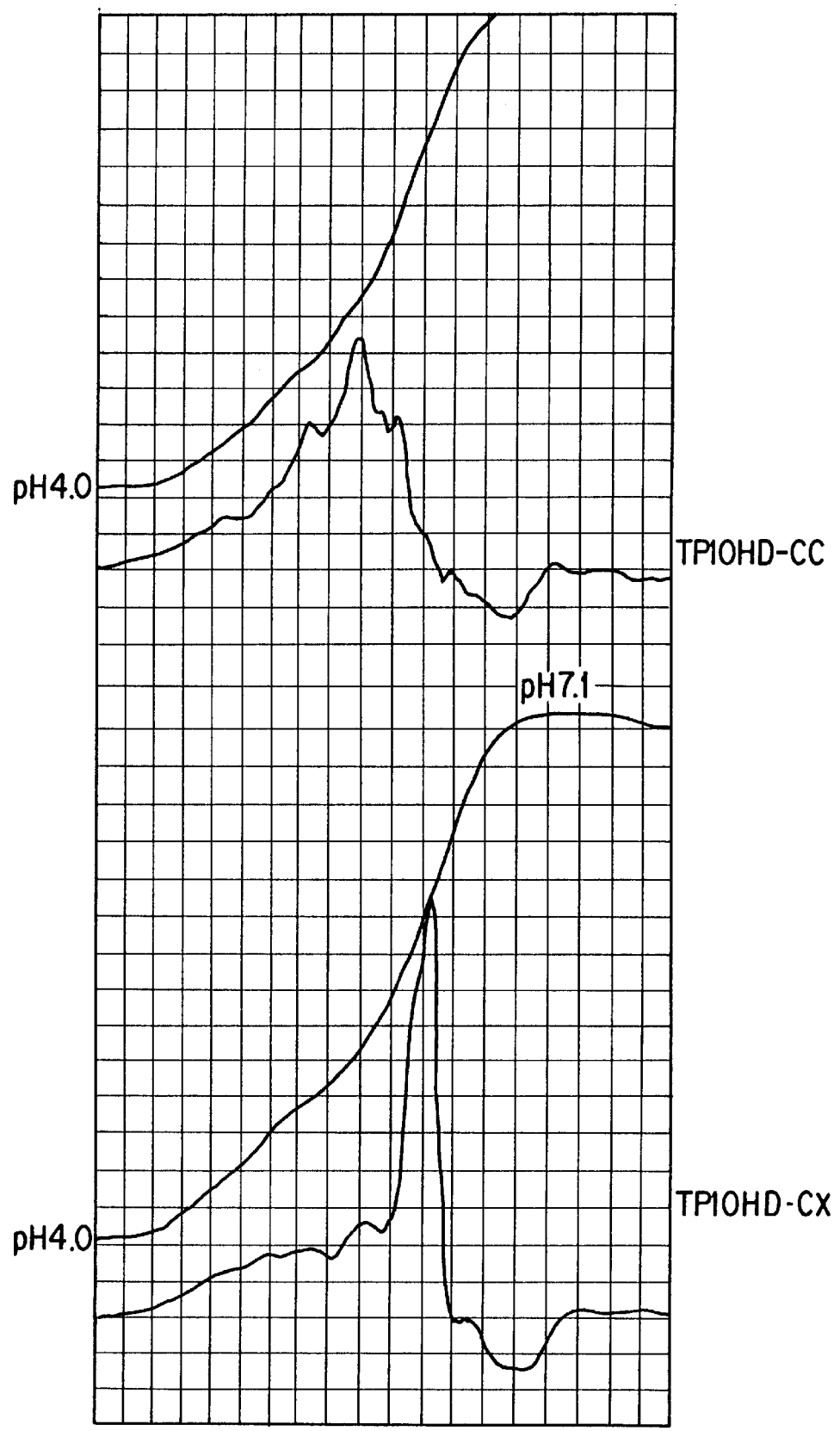
FIG. 6 shows a tracing from a chromatofocusing column for TP10HD-CC (top) and TP10HD-CX (bottom).

FIG. 6 summarizes the results of this experiment. The dominant isoforms in TP10HD-CX have pI's of approximately 6.0 and 5.7, with smaller quantities of material at pI 5.0 and below. In the TP10HD-CC preparation, the pI 5.7 isoform was a minor component; the dominant forms had pI's of 5.1 and 4.8. Integration of the peaks suggests that approximately 40% of the TP10HD-CC preparation had a pI <4.9. Since the quantity of material in the TP10HD-CX preparation with pI <4.9 is so small, it was not possible to accurately assess the proportion of lower pI material in this preparation.

Conclusion

TP10HD-CX was found to have a higher average pI than TP10HD-CC, consistent with a lower content of post-translationally derived acidic groups. However, there was some overlap in the isoform profile between the two TP10HD preparations. The percentage of TP10HD-CC with a low pI (pI <4.9) correlated with the percentage of slowly clearing material from the plasma in pigs (see Example VI). These results are in agreement with the findings described in Example VIII, that glycoforms with the higher levels of terminal sialic acid residues demonstrate a lower pI.

EXAMPLE XI

Functional Activity of the TP10HD Glycoforms: Inhibition of Complement-Mediated Hemolysis in Vitro The various TP10HD glycoforms have comparable in vitro antihemolytic functional activity within the confidence interval of the assay, as shown by the results presented below.

Methods

The hemolysis inhibition assay is based on the ability of solutions of TP10HD to inhibit the lysis of SRBC sensitized with a rabbit polyclonal antibody in the presence of human serum as a complement source and is described in Example VI, above.

Activity is expressed as the concentration of TP10HD giving 50% inhibition of hemolysis, $IH_{50}$, under the standard assay conditions. The lower the concentration of TP10HD, or TP10HD glycoform, yielding 50% inhibition, the more potent the preparation. A range of dilutions of TP10HD or TP10HD glycoform spanning 7.8 to 1000 ng/ml was examined for each sample.

Results

TP10HD-CX demonstrated a typical $IH_{50}$ of 20±7 ng/ml, whereas the value for TP10HD-CC was higher, about 50±3 ng/ml, suggesting that the potency of the preparation containing a significant quantity of weakly cationic, heavily sialylated glycoform was approximately 2-fold lower than the strongly cationic glycoform. TP10HD-CCW had a typical $IH_{50}$ of 44 ng/ml while TP10HD-CCS had $IH_{50}$ values in the range of 27 ng/ml. These results are consistent with the values for the unfractionated preparations TP10HD-CX and TP10HD-CC. Deglycosylation lowered the $IH_{50}$ from 80 ng/ml for TP10HD-CX to 40 ng/ml for TP10HD-CXD.

Conclusion

The intra-assay variability of this assay is in the range of 15–20%, so that the significance of 2-fold differences in $IH_{50}$ values is difficult to interpret, whereas four-fold or greater changes are considered significant. There is therefore no basis for concluding that TP10HD-CC, TP10HD-CCW and TP10HD-CCS differ in their potency in this assay. Increased glycosylation or sialylation of these glycoforms, which markedly increases in vivo plasma half-life, clearly has no major impact on in vitro potency in hemolysis inhibition.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method of delaying transplant rejection in a subject, comprising administering to a subject in need of such treatment a pharmaceutical composition comprising a pharmaceutically acceptable carrier or excipient and a therapeutically effective amount of sCR1 glycoprotein molecules, in which said composition exhibits dominant isoforms of sCR1 glycoprotein molecules which have an isoelectric point, pI, less than or equal to 5.1 as determined by chromatofocusing, and wherein the pI of said dominant isoforms increases after neuraminidase treatment.

2. A method of delaying transplant rejection in a subject, comprising administering to a subject in need of such treatment a pharmaceutical composition comprising a pharmaceutically acceptable carrier or excipient and a therapeutically effective amount of sCR1 glycoprotein molecules, wherein substantially all of the sCR1 glycoprotein molecules in said composition contain one or more complex oligosaccharide structures, wherein at least about 40% of said oligosaccharide structures are terminated with one or more sialic acid residues per oligosaccharide structure.

3. The method of claim 2, wherein at least about 70% of said oligosaccharide structures are terminated with one or more sialic acid residues per oligosaccharide structure.

4. A method of delaying transplant rejection in a subject, comprising administering to a subject in need of such treatment a pharmaceutical composition comprising a pharmaceutically acceptable carrier or excipient and a therapeutically effective amount of sCR1 glycoprotein molecules, in which 70% of all of said sCR1 glycoprotein molecules have an isoelectric point, pI, less than or equal to 5.1 as determined by chromatofocusing, and wherein the pI of said dominant isoforms increases after neuraminidase treatment.

5. A method of delaying transplant rejection in a subject, comprising administering to a subject in need of such treatment a pharmaceutical composition comprising a pharmaceutically acceptable carrier or excipient and a therapeutically effective amount of sCR1 glycoprotein molecules having an average molar ratio of sialic acid to mannose greater than or equal to 0.25.

6. A method according to claim 5, wherein the sCR1 glycoprotein molecules have an average molar ratio of sialic acid to mannose greater than or equal to 0.38.

7. A method according to claim 5, wherein the sCR1 glycoprotein molecules have an average molar ratio of sialic acid to mannose greater than or equal to 0.42.

8. A method according to claim 5, wherein the sCR1 glycoprotein molecules have an average molar ratio of sialic acid to mannose greater than or equal to 0.53.

9. The method according to claim 1, 2, 3, 4, or 5 in which the transplant is a xenograft.

10. The method according to claim 1, 2, 3, 4, or 5 which the transplant is an allograft.

11. The method of claim 1, 2, 3, 4, or 5 wherein said sCR1 glycoprotein molecules comprise the 30 extracellular short consensus repeats of human CR1.

12. A method for making an sCR1 glycoprotein preparation comprising:
   (a) expressing DNA encoding an sCR1 polypeptide in a mammalian host cell in culture under conditions wherein cell growth is not limited by nutrient supply and wherein said host cell is capable of sialylation of oligosaccharide structures;
   (b) recovering a composition comprising a plurality of sCR1 glycoprotein molecules from the culture;
   (c) recovering sCR1 glycoprotein isoforms from the composition to afford a preparation which exhibits dominant sCR1 glycoprotein isoforms having an isoelectric point, pI, less than or equal to 5.1 as determined by chromatofocusing, wherein the pI of said dominant isoforms increases after neuraminidase treatment.

13. A method for making an sCR1 glycoprotein preparation comprising:
   (a) expressing DNA encoding an sCR1 polypeptide in a mammalian host cell in culture under conditions wherein cell growth is not limited by nutrient supply and wherein said host cell is capable of sialylation of oligosaccharide structures;
   (b) recovering a composition comprising a plurality of sCR1 glycoprotein molecules from the culture;
   (c) recovering sCR1 glycoprotein isoforms from the composition to afford a preparation wherein substantially all of the sCR1 glycoprotein molecules contain one or more complex oligosaccharide structures, wherein at least about 40% of said oligosaccharide structures are terminated with one or more sialic acid residues per oligosaccharide structure.

14. The method according to claim 13, wherein at least about 70% of said oligosaccharide structures are terminated with one or more sialic acid residues per oligosaccharide structure.

15. A method for making an sCR1 glycoprotein preparation comprising:
   (a) expressing DNA encoding an sCR1 polypeptide in a mammalian host cell in culture under conditions wherein cell growth is not limited by nutrient supply and wherein said host cell is capable of sialylation of oligosaccharide structures;
   (b) recovering a composition comprising a plurality of sCR1 glycoprotein molecules from the culture;
   (c) recovering sCR1 glycoprotein isoforms from the composition to afford a preparation of sCR1 glycoprotein molecules having an average molar ratio of sialic acid to mannose greater than or equal to 0.25.

16. A method according to claim 15, wherein the sCR1 glycoprotein molecules have an average molar ratio of sialic acid to mannose greater than or equal to 0.38.

17. A method according to claim 15, wherein the sCR1 glycoprotein molecules have an average molar ratio of sialic acid to mannose greater than or equal to 0.42.

18. A method according to claim 15, wherein the sCR1 glycoprotein molecules have an average molar ratio of sialic acid to mannose greater than or equal to 0.53.

19. The method of claim 12, 13, 14, or 15, further comprising:
  (d) isolating sialic acid-containing sCR1 glycoprotein molecules from the preparation obtained in step (c).

20. The method of claim 12, 13, 14, or 15 wherein said sCR1 polypeptide comprises the 30 extracellular short consensus repeats (SCRs) of human CR1.

21. A method for making an sCR1 glycoprotein preparation comprising:
  (a) providing a composition comprising a plurality of sCR1 glycoprotein molecules produced by a mammalian cell; and
  (b) recovering sCR1 glycoprotein isoforms from the composition to afford a preparation which exhibits dominant sCR1 glycoprotein isoforms having an isolelectric point, pI, less than or equal to 5.1 as determined by chromatofocusing, wherein the pI of said dominant isoforms increases after neuraminidase treatment.

22. A method for making an sCR1 glycoprotein preparation comprising:
  (a) providing a composition comprising a plurality of sCR1 glycoprotein molecules produced by a mammalian cell; and
  (b) recovering sCR1 glycoprotein isoforms from the composition to afford a preparation wherein substantially all of the sCR1 glycoprotein molecules contain one or more complex oligosaccharide structures, wherein at least about 40% of said oligosaccharide structures are terminated with one or more sialic acid residues per oligosaccharide structure.

23. The method according to claim 22, wherein at least about 70% of said oligosaccharide structures are terminated with one or more sialic acid residues per oligosaccharide structure.

24. A method for making an sCR1 glycoprotein preparation comprising:
  (a) providing a composition comprising a plurality of sCR1 glycoprotein molecules produced by a mammalian cell; and
  (b) recovering sCR1 glycoprotein isoforms from the composition to afford a preparation of sCR1 glycoprotein molecules having an average molar ratio of sialic acid to mannose greater than or equal to 0.25.

25. A method according to claim 24, wherein the sCR1 glycoprotein molecules have an average molar ratio of sialic acid to mannose greater than or equal to 0.38.

26. A method according to claim 24, wherein the sCR1 glycoprotein molecules have an average molar ratio of sialic acid to mannose greater than or equal to 0.42.

27. A method according to claim 24, wherein the sCR1 glycoprotein molecules have an average molar ratio of sialic acid to mannose greater than or equal to 0.53.

28. The method of claim 21, 22, 23, or 24 wherein said sCR1 glycoprotein molecules comprise the 30 extracellular short consensus repeats (SCRs) of human CR1.

* * * * *